US008894926B2

(12) United States Patent
Hanada et al.

(10) Patent No.: US 8,894,926 B2
(45) Date of Patent: Nov. 25, 2014

(54) STERILIZATION APPARATUS AND STERILIZATION METHOD

(71) Applicants: Canon Marketing Japan Kabushiki Kaisha, Tokyo (JP); Elk Corporation, Osaka (JP); Kabushiki Kaisha Elquest, Chiba (JP)

(72) Inventors: Yasushi Hanada, Chiba (JP); Takashi Koyama, Tokyo (JP)

(73) Assignees: Canon Marketing Japan Kabushiki Kaisha, Tokyo (JP); Elk Corporation, Osaka (JP); Kabushiki Kaisha Elquest, Chiba (JP)

( * ) Notice: Subject to any disclaimer, the term of this patent is extended or adjusted under 35 U.S.C. 154(b) by 113 days.

(21) Appl. No.: 13/645,200

(22) Filed: Oct. 4, 2012

(65) Prior Publication Data

US 2013/0094992 A1 Apr. 18, 2013

(30) Foreign Application Priority Data

Oct. 6, 2011 (JP) ................................ 2011-222383

(51) Int. Cl.
| | |
|---|---|
| A61L 9/00 | (2006.01) |
| A61L 2/00 | (2006.01) |
| C25B 5/00 | (2006.01) |
| C25B 15/00 | (2006.01) |
| F26B 3/34 | (2006.01) |
| F26B 3/00 | (2006.01) |
| A61L 2/16 | (2006.01) |
| C01B 13/02 | (2006.01) |
| A61L 2/20 | (2006.01) |
| C01B 15/013 | (2006.01) |

(52) U.S. Cl.
CPC ............ *A61L 2/16* (2013.01); *C01B 13/0214* (2013.01); *A61L 2202/11* (2013.01); *A61L 2/208* (2013.01); *C01B 15/013* (2013.01); *A61L 2202/14* (2013.01)

USPC ............... 422/28; 422/22; 422/32; 422/105; 422/119; 422/305; 204/155; 204/234; 34/250; 34/443; 34/524

(58) Field of Classification Search
CPC ........ A01N 1/0215; A61L 2/00; A61L 2/186; A61L 2/208; A61L 2/22; A61L 9/015; A61K 8/22; B05B 1/28
USPC ............... 422/1, 3–5, 22, 26, 28, 32–33, 105, 422/119, 121, 123–124, 186.04, 298–299, 422/305–307; 204/155, 234; 34/250, 443, 34/524
See application file for complete search history.

(56) References Cited

U.S. PATENT DOCUMENTS

| | | | |
|---|---|---|---|
| 6,936,434 B2 * | 8/2005 | McDonnell et al. | ............ 435/31 |
| 2013/0004384 A1 | 1/2013 | Yoo | |

FOREIGN PATENT DOCUMENTS

KR 100985801 B1 10/2010

Primary Examiner — Monzer R Chorbaji
(74) Attorney, Agent, or Firm — Canon USA, Inc. IP Division

(57) ABSTRACT

It is to provide a mechanism where a sterilization process using a concentrated sterilizing agent and a sterilization process using a sterilizing agent that has not been concentrated can be switched without changing the sterilization process.

In the case where the concentrated mode is received by receiving means the transfer of the sterilizing agent to the concentration chamber is controlled according to a first timing, and in the case where the non-concentrated mode is received by the receiving means, the transfer of the sterilizing agent to the concentration chamber is controlled according to a second timing, wherein the first timing is different from the second timing.

15 Claims, 15 Drawing Sheets

STERILIZATION APPARATUS AND STERILIZATION METHOD

BACKGROUND OF THE INVENTION

1. Field of the Invention

The present invention relates to a sterilization apparatus and a sterilization method. In particular, the invention relates to a sterilization apparatus and sterilization method, which can be switched between a sterilization process using a concentrated sterilizing agent and a sterilization process using a sterilizing agent that has not been concentrated.

2. Description of the Related Art

Since there is a concern that pathogens may become attached to medical equipment such as syringes and surgical tools during use and that this may have an adverse effect on the human body, medical equipment cannot be reused in cases where it is not sterilized after use. For this reason, there are sterilization apparatuses which perform a sterilization process on target objects, such as medical equipment, requiring sterilization.

A sterilization apparatus and a sterilization method have been proposed in which target objects are sterilized using hydrogen peroxide as a sterilizing agent (for example, Japanese Unexamined Patent Application Publication No. 08-505787).

When sterilizing target objects with a sterilization apparatus, to improve the sterilizing effect, sterilization is performed by concentrating a sterilizing agent and using the concentrated sterilizing agent. However, depending on the target object for sterilization, a target object may be broken down or deteriorated when the target object is sterilized using a concentrated sterilizing agent. For such target objects for sterilization, a normal sterilizing agent that has not been concentrated is used for sterilization.

However, conventionally, when sterilization is carried out using a concentrated sterilizing agent, a sterilization apparatus dedicated to sterilization using a concentrated sterilizing agent is required. Further, when sterilization is carried out using a normal sterilizing agent that has not been concentrated, a sterilization apparatus dedicated to sterilization using a sterilizing agent that has not been concentrated and which has no sterilizing agent concentration mechanism is required.

In addition, to implement these functions in one sterilization apparatus, the sterilization apparatus must be provided with a sterilization process dedicated to sterilization using a sterilizing agent that has not been concentrated as well as a sterilization process dedicated to sterilization using a concentrated sterilizing agent. Thus, in addition to an increase in cost, the size of the sterilization apparatus may also increase.

SUMMARY OF THE INVENTION

An object of the present invention is to provide a mechanism which can switch between a sterilization process using a concentrated sterilizing agent and a sterilization process using a sterilizing agent that has not been concentrated.

According to an aspect of the present invention, there is provided sterilization apparatus as set out in claims 1 to 12.

According to another aspect of the present invention, a sterilization method is provided as set out in claim 13.

According to a further aspect of the present invention, there is provided a computer program as set out in claim 14.

Further features and aspects of the present invention will become apparent from the following detailed description of embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Various embodiments, features, and aspects of the invention will be described in detail below with reference to the drawings.

With reference to the accompanying drawings, the sterilization apparatus of the present invention and the sterilization method will be described.

First, the external appearance of the sterilization apparatus according to the invention will be described using FIG. 1.

Figure 1:
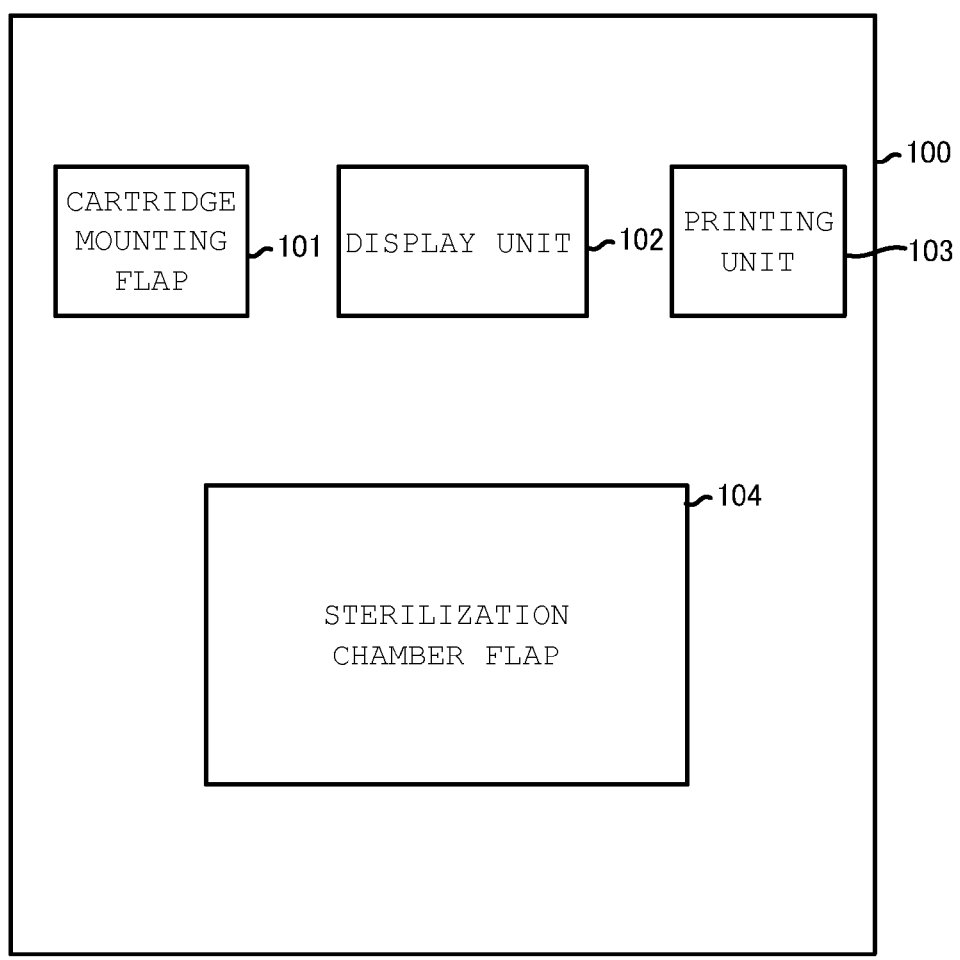
FIG. 1 is a diagram of an external appearance of a sterilization apparatus according to an embodiment of the invention viewed from the front.

FIG. 1 is a diagram of the external appearance of a sterilization apparatus according to the invention viewed from the front.

A sterilization apparatus 100 according to the invention includes a cartridge mounting flap 101, a display unit 102, a printing unit 103, and a sterilization chamber flap 104.

The cartridge mounting flap 101 is a flap for mounting a cartridge, which is a container filled with a sterilizing agent (hydrogen peroxide or liquid hydrogen peroxide solution). When the cartridge mounting flap 101 is opened, there is a cartridge mounting place, and it is possible for a user to install the cartridge at the place.

The display unit 102 is a touch panel display screen such as a liquid crystal display.

The printing unit 103 is a printer which prints a history of sterilization processes and sterilization results on printing paper as appropriate.

The sterilization chamber flap 104 is a flap for inserting objects for sterilization into a sterilization chamber to sterilize target objects (objects for sterilization) such as equipment for medical treatment. When the sterilization chamber flap 104 is opened, there is a sterilization chamber, and it is possible to insert target objects for sterilization into the sterilization chamber by inserting objects for sterilization and closing the sterilization chamber flap 104.

The sterilization chamber is a housing with a predetermined capacity. It is possible to maintain the air pressure inside the sterilization chamber from atmospheric pressure up to vacuum pressure. In addition, the temperature inside the sterilization chamber is maintained at a temperature in a predetermined range during the sterilization process.

Figure 2:
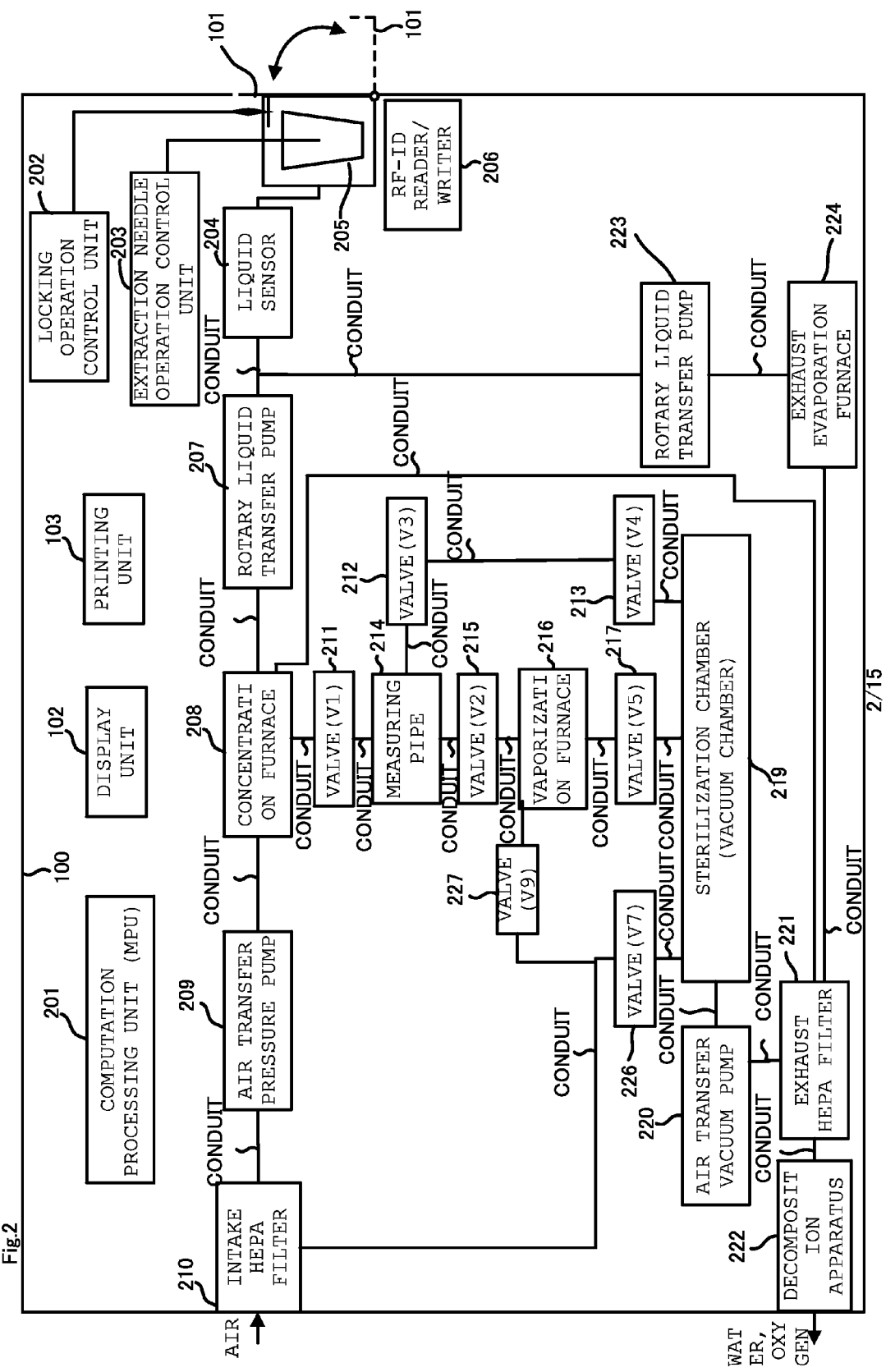
FIG. 2 is a diagram illustrating a configuration of the hardware of the sterilization apparatus according to an embodiment of the invention.

<Description of FIG. 2>

Next, an example of a configuration of the hardware of the sterilization apparatus according to the invention will be described with reference to FIG. 2.

FIG. 2 is a diagram illustrating a configuration of the hardware of the sterilization apparatus according to an embodiment of the invention.

The sterilization apparatus 100 according to this embodiment comprises a computation processing unit 201 (such as an MPU), a display unit 102, a printing unit 103, a locking operation control unit 202, an extraction needle operation control unit 203, a cartridge mounting flap 101, a liquid sensor 204, cartridges 205, and an RF-ID reader/writer 206, a rotary liquid transfer pump 207, a concentration furnace 208, an air transfer pressure pump 209, an intake HEPA filter 210, a valve (V1) 211, a valve (V3) 212, a valve (V4) 213, a measuring pipe 214, a valve (V2) 215, a vaporization furnace 216, a valve (V5) 217, a valve (V9) 227, a valve (V7) 226, a sterilization chamber (also referred to as a vacuum chamber) 219, an air transfer vacuum pump 220, an exhaust HEPA filter 221, a sterilizing agent decomposition apparatus 222, a rotary liquid transfer pump 223, and an exhaust evaporation furnace 224.

The computation processing unit 201 (such as an MPU) performs a computation process and controls each item of hardware configuring the sterilization apparatus 100.

Since the display unit 102, the printing unit 103 and the cartridge mounting flap 101 have been already described using FIG. 1, description thereof will not be repeated.

The locking operation control unit 202, is a portion that performs a locking and unlocking operation of the cartridge mounting flap 101, prevents the cartridge mounting flap 101 from opening by locking the cartridge mounting flap 101, and further, makes it possible to open the cartridge mounting flap 101 by unlocking the cartridge mounting flap 101.

The cartridge 205 is a sealed container filled with sterilizing agent (hydrogen peroxide or liquid hydrogen peroxide). In addition, the lower side of the cartridge 205 is provided with a RF-ID storage medium. The storage medium stores a serial number as information that identifies the cartridge, the date of manufacture of the cartridge, the date and time at which the cartridge was first used in a sterilization apparatus (date and time of first use) and the remaining amount of sterilizing agent that the cartridge contains.

The extraction needle operation control unit 203 is a portion that operates an extraction needle (injection needle) for suctioning the sterilizing agent in the cartridge and to pierce the cartridge with the extraction needle from above.

In other words, in the case of piercing the cartridge with the extraction needle (injection needle) for suctioning the sterilizing agent in the cartridge from above, it is possible to pierce the cartridge with the extraction needle from above by pointing the extraction needle toward the cartridge and lowering the extraction needle from above the cartridge. In addition, in a case of extracting the extraction needle from the cartridge, it is possible to extract the extraction needle from the cartridge by raising the extraction needle.

The liquid sensor 204 is a device that detects whether the liquid sterilizing agent in the cartridge 205 is passing through the pipe (conduit pipe) which leads from the extraction needle (injection needle) to the rotary liquid transfer pump 223 and the rotary liquid transfer pump 207. Specifically, it is possible to detect whether the sterilizing agent is passing through the pipe, from a spectrum obtained by irradiating the pipe with infrared light.

The RF-ID reader/writer 206 is a device that can read the serial number, the date of manufacture, the date and time of first use and the remaining amount of sterilizing agent from the RF-ID fitted to the bottom of the cartridge 205. Further, the RF-ID reader/writer 206 is a device that can write the date and time of first use and the remaining amount of sterilizing agent in the RF-ID fitted to the bottom of the cartridge 205. In addition, by installing the RF-ID reader/writer 206 at the bottom of the cartridge mounting location behind the cartridge mounting flap 101, it is possible to read the RF-ID fitted to the bottom of the cartridge 205, and to write data such as the date and time of first use and the remaining amount of sterilizing agent in the RF-ID.

The rotary liquid transfer pump 207 leads to the concentration furnace 208 via a conduit pipe, and in addition leads to the liquid sensor 204 via a conduit pipe. The liquid sterilizing agent in the cartridge 205 is suctioned using the rotary liquid transfer pump 207 and the sterilizing agent is transferred through a conduit pipe to the concentration furnace 208. In addition, the rotary liquid transfer pump 207 is capable of suctioning a predetermined amount of a sterilizing agent from the cartridge 205 in conjunction with the liquid sensor 204.

The concentration furnace 208 leads to the rotary liquid transfer pump 207, the air transfer pressure pump 209, the measuring pipe 214, and the exhaust HEPA filter 221 respectively via conduit pipes. While the concentration furnace 208 will be described later in FIG. 10, a sterilizing agent fed through a conduit pipe from the rotary liquid transfer pump 207 is concentrated therein by heating with a heater, thereby evaporating (vaporizing) moisture and the like contained in the sterilizing agent. In addition, the gasified water is pushed out to a conduit pipe which leads to the exhaust HEPA filter 221, by air fed through a conduit pipe from the air transfer pressure pump 209 and is evacuated from the inside of the concentration furnace 208. In addition, the valve (V1) 211 is provided in a conduit pipe between the measuring pipe 214 and the concentration furnace 208.

The air transfer pressure pump 209 leads to the concentration furnace 208 and the intake HEPA filter 210 respectively via conduit pipes. In the air transfer pressure pump 209, the external air of the sterilization apparatus 100 is transferred through the intake HEPA filter 210 to the concentration furnace 208 using a conduit pipe of the intake HEPA filter 210.

The intake HEPA filter 210 leads to the air transfer pressure pump 209, the sterilization chamber 219, and the vaporization furnace 216 respectively via conduit pipes. The intake HEPA filter 210 filters dust, dirt and bacteria from external air drawn from outside the sterilization apparatus 100 using a HEPA (High Efficiency Particulate Air Filter) filter, thereby cleaning the air. The cleaned air is transferred to the concentration furnace 208 through a conduit pipe by the air transfer pressure pump 209.

In addition, the cleaned air is fed into the vaporization furnace 216 using a conduit pipe of the vaporization furnace 216, and fed into the sterilization chamber 219 using a conduit pipe of the sterilization chamber 219. In other words, the intake HEPA filter 210 conducts external air outside the sterilization apparatus 100. Therefore, the conduit pipe between the air transfer pressure pump 209 and the intake HEPA filter 210, the conduit pipe between the sterilization chamber 219 and the intake HEPA filter 210 and the conduit pipe between the vaporization furnace 216 and the intake HEPA filter 210 conduct external air through the intake HEPA filter 210.

In addition, the valve (V9) 227 is provided in a conduit pipe between the vaporization furnace 216 and the intake HEPA filter 210. In addition, the valve (V7) 226 is provided in a conduit pipe between the intake HEPA filter 210 and the sterilization chamber 219.

The valve (V1) 211 is a valve which is provided in the conduit pipe between the concentration furnace 208 and the measuring pipe 214, and opening the valve allows fluid flow between the concentration furnace 208 and the measuring pipe 214 through the conduit pipe. By closing the valve, fluid flow between the concentration furnace 208 and the measuring pipe 214 through the conduit pipe is prevented.

The valve (V3) 212 is a valve which is provided in the conduit pipe between the measuring pipe 214 and the sterilization chamber 219, and opening the valve allows fluid flow between the measuring pipe 214 and the sterilization chamber 219 through the conduit pipe. By closing the valve, fluid flow between the measuring pipe 214 and the sterilization chamber 219 through the conduit pipe is prevented. This valve is provided close to the measuring pipe 214, and is provided in a position closer to the measuring pipe 214 side than at least the valve (V4) that will be described later.

The valve (V4) 213 is a valve which is provided in the conduit pipe between the measuring pipe 214 and the sterilization chamber 219, and opening the valve allows fluid flow between the measuring pipe 214 and the sterilization chamber 219 through the conduit pipe. By closing the valve, fluid flow between the measuring pipe 214 and the sterilization chamber 219 through the conduit pipe is prevented. This valve is provided close to the sterilization chamber 219, and is provided in a position closer to the sterilization chamber 219 side than at least the valve (V3) that will be described later.

In this exemplary embodiment, connection of the conduit pipe between the measuring pipe and the sterilization chamber is enabled and prevented by opening and closing the valve (V4) 213 and the valve (V3) 212. However, it is possible to allow and prevent connection of the conduit pipe between the measuring pipe and the sterilization chamber by opening and closing either the valve (V4) 213 or the valve (V3) 212.

More specifically, it is also possible to allow and prevent connection of the conduit pipe between the measuring pipe and the sterilization chamber by only providing one of the valve (V4) 213 and the valve (V3) 212 and performing opening and closing that valve.

The measuring pipe 214 is connected to respective conduit pipes arranged between the measuring pipe 214 and the concentration furnace 208, the vaporization furnace 216 or the sterilization chamber 219.

In the measuring pipe 214, the sterilizing agent flows from the concentration furnace 208 when the valve (V1) 211 is opened. Unnecessary air sucked in from inside the cartridge 205 is removed by the measuring pipe 214 when the valve (V3) 212 and the valve (V4) 213 are opened and/or unnecessary air that flows into the concentration furnace 208 from the intake HEPA filter 210 and into the measuring pipe 214 from the concentration furnace 208. The measuring pipe 214 will be described in more detail later using FIG. 10.

The valve (V2) 215 is a valve which is provided in the conduit pipe between the measuring pipe 214 and the vaporization furnace 216, and opening the valve allows fluid flow between the measuring pipe 214 and the vaporization furnace 216 through the conduit pipe. By closing the valve, fluid flow between the measuring pipe 214 and the vaporization furnace 216 through the conduit pipe is prevented.

The vaporization furnace 216 is connected via conduit pipes to the measuring pipe 214, the intake HEPA filter 210 or the sterilization chamber 219. The vaporization furnace 216 is an example of a vaporization chamber.

In the vaporization furnace 216, the sterilizing agent is gasified by depressurization by the air transfer vacuum pump 220.

The valve (V5) 217 is a valve which is provided in the conduit pipe between the vaporization furnace 216 and the sterilization chamber 219. By opening the valve, fluid flow between the vaporization furnace 216 and the sterilization chamber 219 through the conduit pipe is enabled. By closing the valve fluid flow between the vaporization furnace 216 and the sterilization chamber 219 through the conduit pipe is prevented.

The valve (V9) 227 is a valve which is provided in the conduit pipe between the vaporization furnace 216 and the intake HEPA filter 210. By opening the valve, fluid flow between the vaporization furnace 216 and the intake HEPA filter 210 through the conduit pipe is enabled. By closing the valve, fluid flow between the vaporization furnace 216 and the intake HEPA filter 210 through the conduit pipe is prevented. In other words, the valve (V9) 227 is a valve which allows and prevents communication between the vaporization furnace 216 and external air (atmosphere).

The valve (V7) 226 is a valve which is provided in the conduit pipe between the sterilization chamber 219 and the intake HEPA filter 210. By opening the valve, fluid flow between the sterilization chamber 219 and the intake HEPA filter 210 through the conduit pipe is enabled. By closing the valve, fluid flow between the sterilization chamber 219 and the intake HEPA filter 210 through the conduit pipe is prevented. In other words, the valve (V7) 226 is a valve which allows and prevents connection between the sterilization chamber 219 and external air (atmosphere).

The sterilization chamber (also referred to as the vacuum chamber) 219 was described with reference to FIG. 1 which is a housing with a predetermined capacity. The sterilization chamber sterilizes target objects such as, for example, equipment for medical treatment. It is possible to maintain the air pressure inside the sterilization chamber from atmospheric pressure up to vacuum pressure. The temperature inside the sterilization chamber is maintained at a temperature in a predetermined range during the sterilization process.

In addition, pressure sensors are provided in the sterilization chamber 219, and it is possible to measure the pressure (air pressure) inside the sterilization chamber 219 using the pressure sensors. The sterilization apparatus 100 determines whether the pressure (air pressure) of the sterilization chamber 219 and the like are predetermined air pressures using the air pressure inside the sterilization chamber 219 measured by using the pressure sensors.

The air transfer vacuum pump 220 is a device that suctions gaseous matter from the spaces inside the sterilization chamber 219, the vaporization furnace 216, the measuring pipe 214, the conduit pipe between the measuring pipe 214 and the vaporization furnace 216, the conduit pipe between the vaporization furnace 216 and the sterilization chamber 219 and the conduit pipe between the measuring pipe 214 and the sterilization chamber 219. It depressurizes the respective spaces by creating a vacuum state (the state of a space which is filled with gaseous matter at a pressure lower than atmospheric pressure).

The air transfer vacuum pump 220 leads to the space between sterilization chamber 219 via a conduit pipe and leads to the exhaust HEPA filter 221 via a conduit pipe.

The exhaust HEPA filter 221 leads to the air transfer vacuum pump 220 via a conduit pipe. In addition, the exhaust HEPA filter 221 leads to the exhaust evaporation furnace 224 via a conduit pipe. In addition, the exhaust HEPA filter 221 leads to the sterilizing agent decomposition apparatus 222 via a conduit pipe. In addition, the exhaust HEPA filter 221 leads to the concentration furnace 208 via a conduit pipe.

The exhaust HEPA filter 221 filters dust, dirt and bacteria in the gaseous matter transferred from the conduit pipe with the air transfer vacuum pump 220 using a HEPA (High Efficiency Particulate Air Filter) filter, thereby cleaning the gaseous matter suctioned from the sterilization chamber 219 and the like by the air transfer vacuum pump 220. Further, the cleaned gaseous matter is passed through the conduit pipe between the sterilizing agent decomposition apparatus 222 and the exhaust HEPA filter 221 and is transferred to the sterilizing agent decomposition apparatus 222. Molecules of sterilizing agent contained in the gaseous matter are decomposed by the sterilizing agent decomposition apparatus 222, and the molecules after decomposition are released to the outside of the sterilization apparatus 100.

In addition, the exhaust HEPA filter 221 cleans the gaseous matter evacuated from the concentration furnace 208 using the conduit pipe between the concentration furnace 208 and the exhaust HEPA filter 221. This gaseous matter is gasified water of the sterilizing agent which is heated in the concentration furnace 208. However, since it contains small amounts of sterilizing agent, it is transferred through the conduit pipe between the sterilizing agent decomposition apparatus 222 and the exhaust HEPA filter 221 to the sterilizing agent decomposition apparatus 222. Further, molecules of sterilizing agent contained in the gaseous matter are decomposed by the sterilizing agent decomposition apparatus 222, and the molecules after decomposition are released to the outside of the sterilization apparatus 100.

In addition, the exhaust HEPA filter 221 cleans the gasified sterilizing agent that is transferred through the conduit pipe between the exhaust evaporation furnace 224 and the exhaust HEPA filter 221 from the exhaust evaporation furnace 224. Further, the cleaned sterilizing agent (gaseous matter), is transferred through the conduit pipe between the sterilizing agent decomposition apparatus 222 and the exhaust HEPA filter 221 to the sterilizing agent decomposition apparatus 222. Molecules of sterilizing agent contained in the gaseous matter are decomposed by the sterilizing agent decomposition apparatus 222, and the molecules after decomposition are released to the outside of the sterilization apparatus 100.

The sterilizing agent decomposition apparatus 222 leads to the exhaust HEPA filter 221 via a conduit pipe. The sterilizing agent decomposition apparatus 222 decomposes molecules of sterilizing agent contained in gaseous matter transferred from the conduit pipe between the sterilizing agent decomposition apparatus 222 and the exhaust HEPA filter 221, and the molecules after decomposition are released to the outside of the sterilization apparatus 100.

In the sterilizing agent decomposition apparatus 222, for example, in a case where the sterilizing agent is hydrogen peroxide or hydrogen peroxide solution, it is possible to decompose gasified hydrogen peroxide into water and oxygen using manganese dioxide as a catalyst.

The rotary liquid transfer pump 223 leads to the exhaust evaporation furnace 224 via a conduit pipe, and further, leads to the liquid sensor 204 via a conduit pipe.

The rotary liquid transfer pump 223 suctions all of the liquid sterilizing agent in the cartridge 205, and the sterilizing agent that is transferred through the conduit pipe between the liquid sensor 204 and rotary liquid transfer pump 223, is transferred through the conduit pipe between the rotary liquid transfer pump 223 and the exhaust evaporation furnace 224 to the exhaust evaporation furnace 224.

The exhaust evaporation furnace 224 leads to the rotary liquid transfer pump 223 via a conduit pipe, and further, leads to the exhaust HEPA filter 221 via a conduit pipe.

The exhaust evaporation furnace 224 heats all of the liquid sterilizing agent in the cartridge 205 transferred through the conduit pipe between the rotary liquid transfer pump 223 and the exhaust evaporation furnace 224 using a heater fitted to the exhaust evaporation furnace 224, and all of the sterilizing agent is gasified. Further, the gasified sterilizing agent is transferred through the conduit pipe between the exhaust HEPA filter 221 and the exhaust evaporation furnace 224 to the exhaust HEPA filter 221.

Figure 4A:
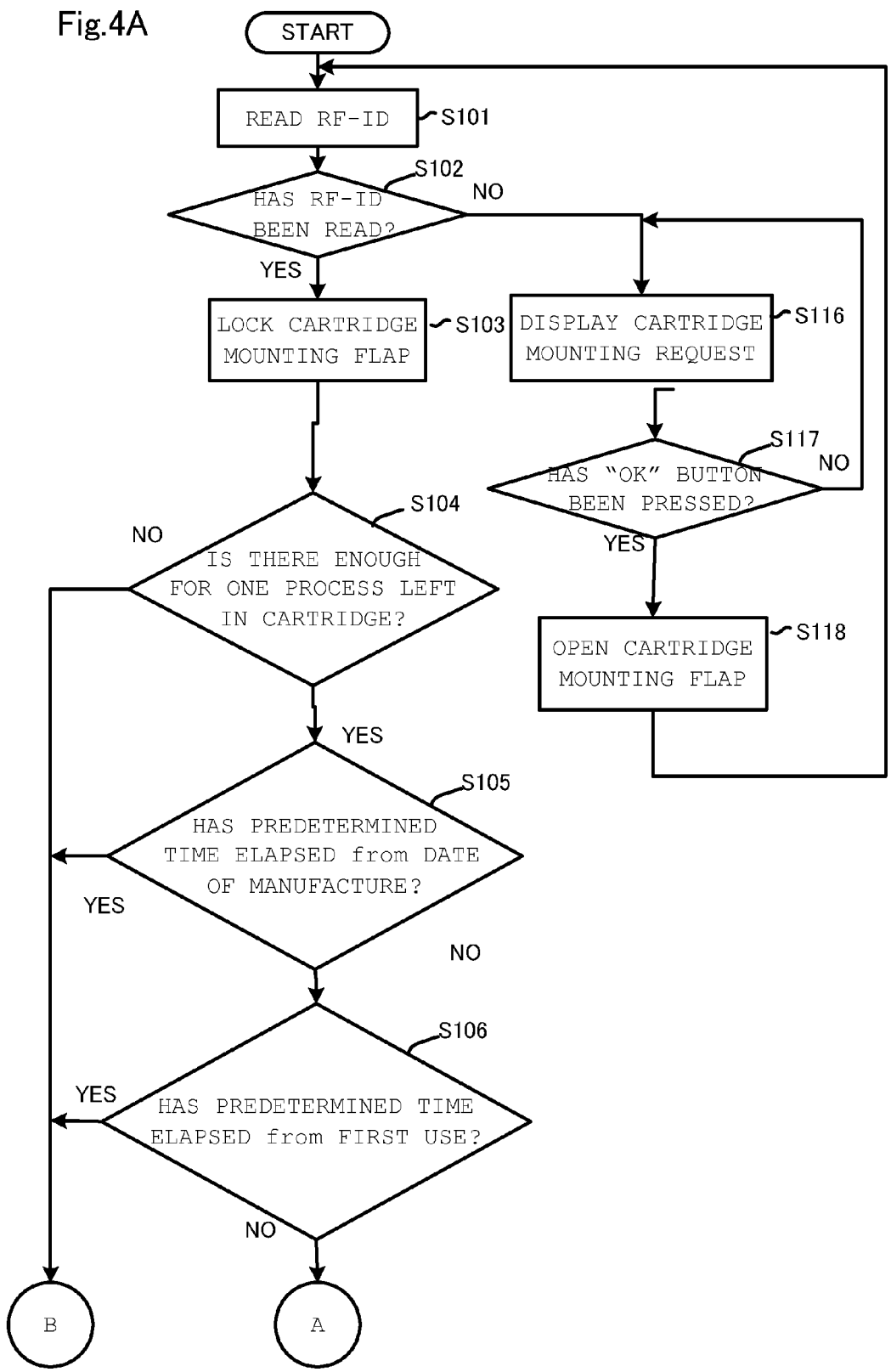
FIG. 4A and FIG. 4B are diagrams illustrating each step of a sterilization process carried out by the sterilization apparatus according to an embodiment of the invention.
Figure 4B:
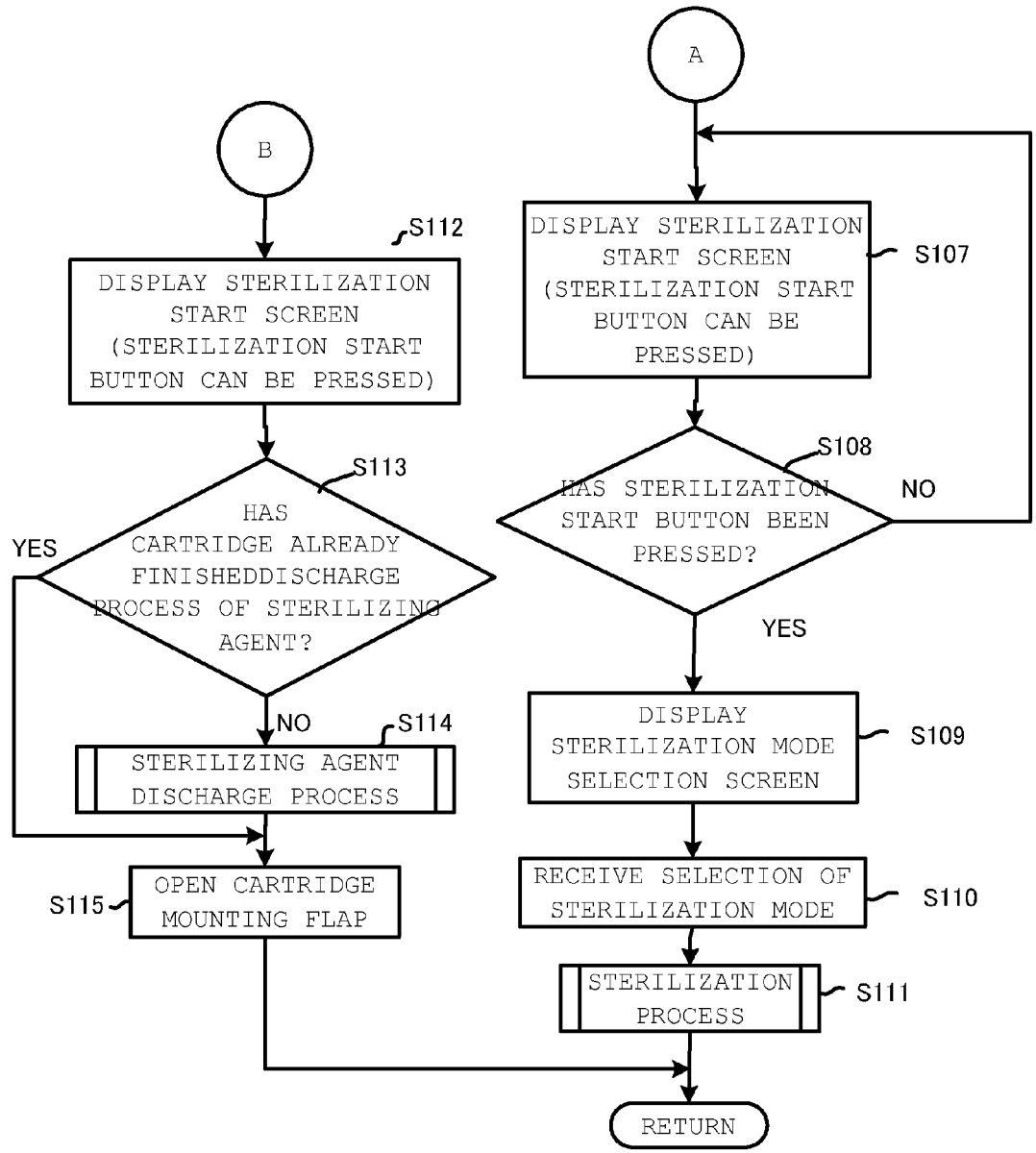

<Description of FIG. 4A and FIG. 4B>

Next, an example of each step of the sterilization process of the sterilization apparatus according to the present invention will be described using FIG. 4A and FIG. 4B.

Each step (process) illustrated in FIG. 4A and FIG. 4B is performed by controlling the operation of each device in the sterilization apparatus using the computation processing unit 201 of sterilization apparatus 100.

FIGS. 4A and 4B are diagrams illustrating an example of each step of the sterilization process of the sterilization apparatus according to an embodiment of the present invention.

In the sterilization apparatus 100, in step S101, when power is turned on, at first, the RF-ID reader/writer 206 reads data from the RF-ID (storage medium) which is provided at the bottom of the cartridge 205.

In step S101, data such as a serial number as information that identifies the cartridge, the date of manufacture of the cartridge, the date and time at which the cartridge was first used in the sterilization apparatus (date and time of first use) and the remaining amount of sterilizing agent that the cartridge contains, is read from the RF-ID (storage medium). More specifically, the serial number, the date of manufacture, the date and time of first use, and the remaining amount of sterilizing agent are stored in the RF-ID (storage medium) that is provided on the cartridge 205 in advance.

Next, in a case where it has been determined that data has been read from the RF-ID in step S101 (YES in step S102), the sterilization apparatus 100 determines that a cartridge is installed in the cartridge mounting place inside the sterilization apparatus 100 and locks the cartridge mounting flap 101 in step S103.

Further, the sterilization apparatus 100 determines whether there is a predetermined amount (for example, 8 ml) of sterilizing agent for one sterilization operation in the cartridge. Specifically, the sterilization apparatus 100 determines whether the remaining amount of sterilizing agent obtained from the RF-ID is greater than a predetermined amount for one sterilization operation. More specifically, in a case where the remaining amount of sterilizing agent is determined to be greater than a predetermined amount for one sterilization operation, it is determined that there is a predetermined amount of sterilizing agent (sufficient Sterilization process can be performed) for one sterilization operation in the cartridge (YES in step S104) and the process of step S105 is performed. On the other hand, in a case where the remaining amount of sterilizing agent is determined to be less than the predetermined amount (for example, 8 ml) for one sterilization operation, it is determined there is not a predetermined amount of sterilizing agent (sufficient sterilization process cannot be performed) for one sterilization operation in the cartridge (NO in step S104) and the process of step S112 is performed.

In step S105, the sterilization apparatus 100 determines whether a predetermined period of time (for example, 13 months) has passed since the date of manufacture of the cartridge obtained from the RF-ID.

Further, in a case where it is determined that the predetermined period of time has passed since the date of manufacture (YES in step S105), it is determined that a sufficient sterilization process cannot be executed and the process of step S112 is performed. On the other hand, in a case where it is determined that the predetermined period has not passed since the date of manufacture (NO in step S105), it is determined that a sufficient sterilization process can be executed and the process of step S106 is performed.

In step S106, the sterilization apparatus 100 determines whether a predetermined period of time (for example, 2 weeks) has passed since the date and time of first use obtained from the RF-ID.

Further, in a case where it is determined that the predetermined period of time has passed since the date and time of first use obtained from the RF-ID (YES in step S106), it is determined that a sufficient sterilization process cannot be executed and the process of step S112 is performed. On the other hand, in a case where it is determined that the predetermined period of time has not passed (NO in step S106), it is determined that a sufficient sterilization process can be executed and the process of step S107 is performed.

In step S107, the sterilization apparatus 100 displays a sterilization start screen (301 in FIG. 3) on the display unit 102.

Figure 3:
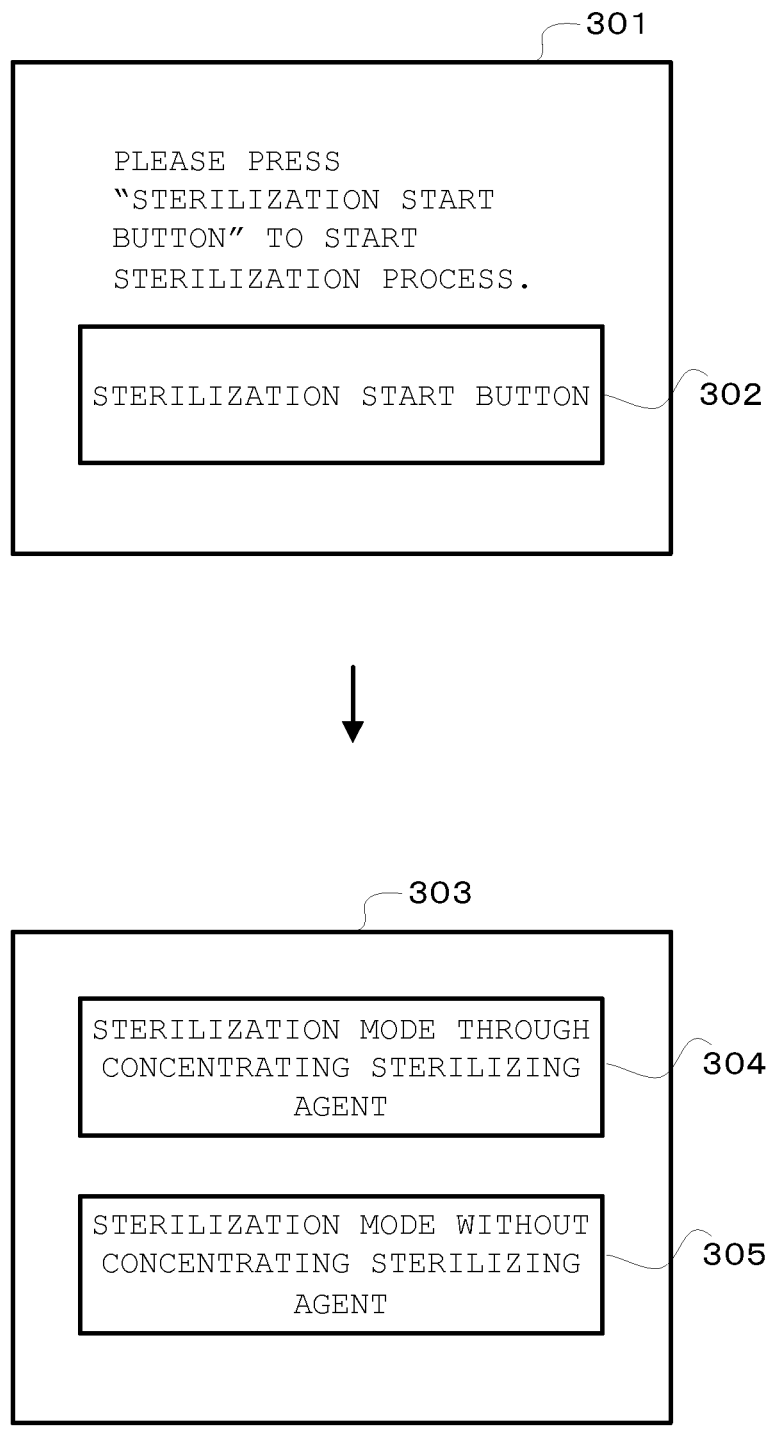
FIG. 3 is a diagram illustrating a screen displayed on a display unit of the sterilization apparatus.

FIG. 3 is a diagram illustrating an example screen that is displayed on the display unit 102 of the sterilization apparatus 100.

A "Start sterilization button" is displayed on the sterilization start screen 301. The "Start sterilization button" 302 on the sterilization start screen 301 displayed in step S107, is operable by a user (active).

Further, when the "Start sterilization button" 302 is pressed by a user (YES in step S108), the sterilization apparatus 100 displays a sterilization mode selection screen (303 in FIG. 3) on the display unit 102.

A "Concentrate sterilizing agent and perform sterilization mode" button 304 and a "Perform sterilization without concentrating sterilizing agent mode" button 305 are displayed on the sterilization mode selection screen 303.

The sterilization apparatus 100 receives a selection from a user of either the "Concentrate sterilizing agent and perform sterilization mode" button 304 or the "Perform sterilization without concentrating sterilizing agent mode" button 305 in step S110, and performs a sterilization process according to the mode of the button selected by the user in step S111. Details of the sterilization processes in step S111 will be described later using FIG. 5.

In this manner, according to the instruction of a user, it is possible to switch the mode which performs a sterilization process in one sterilization apparatus. More specifically, in a case where the "Concentrate sterilizing agent and perform sterilization mode" button 304 is pressed by a user, the sterilizing agent is concentrated and a sterilization process is performed, and in a case where the "Perform sterilization without concentrating sterilizing agent mode" button 305 is pressed by a user, the sterilizing agent is not concentrated and a sterilization process is performed.

Further, when the sterilization process in step S111 ends, the sterilization apparatus 100 returns the process to step S101.

In addition, in step S112, the sterilization apparatus 100 displays the sterilization start screen (301 in FIG. 3) on the display unit 102. However, the "Start sterilization button" 302 on the sterilization start screen (301 in FIG. 3) displayed in step S112, is displayed is inoperable and is preferably displayed in manner that indicates it cannot be pressed by a user ("Start sterilization button" 302 is not active). Therefore, it is possible to ensure that an instruction to start the sterilization process by a user is not accepted.

In addition, in step S113, the sterilization apparatus 100 determines whether the cartridge installed in the cartridge mounting location is a cartridge from which the sterilizing agent has already been fully discharged, by using the serial number obtained in from the RF-ID in step S101. Specifically, serial numbers that identify cartridges from which the sterilizing agent has already been fully discharged are stored in the memory (storage unit) of the sterilization apparatus 100, and it is determined whether the cartridge currently installed in the sterilization apparatus 100 is a cartridge from which the sterilizing agent has already been fully discharged by determining whether the serial number obtained from the RF-ID in step S101 matches a serial number stored in memory (storage unit).

At this point, in a case where it is determined that the cartridge currently installed in the sterilization apparatus 100 is a cartridge from which the sterilizing agent has already been fully discharged (YES in step S113), the process of step S115 is performed. On the other hand, in a case where it is determined that from the cartridge, the sterilizing agent has already been fully discharged (NO in step S113), all of the remaining liquid sterilizing agent in the cartridge is taken up and a decomposition process is carried out. The sterilizing agent is released to the outside of the sterilization apparatus 100 (a sterilizing agent discharge process in step S114), and thereafter, the process of step S115 is performed. The details of the discharge process of step S114 will be described later using FIG. 9.

When the process of step S114 is performed, the serial number read in step S101 is stored in the memory (storage unit) of the sterilization apparatus 100 as a serial number that identifies a cartridge from which the sterilizing agent has already been fully discharged.

In step 115, the sterilization apparatus 100 unlocks the cartridge mounting flap 101.

Figure 11:
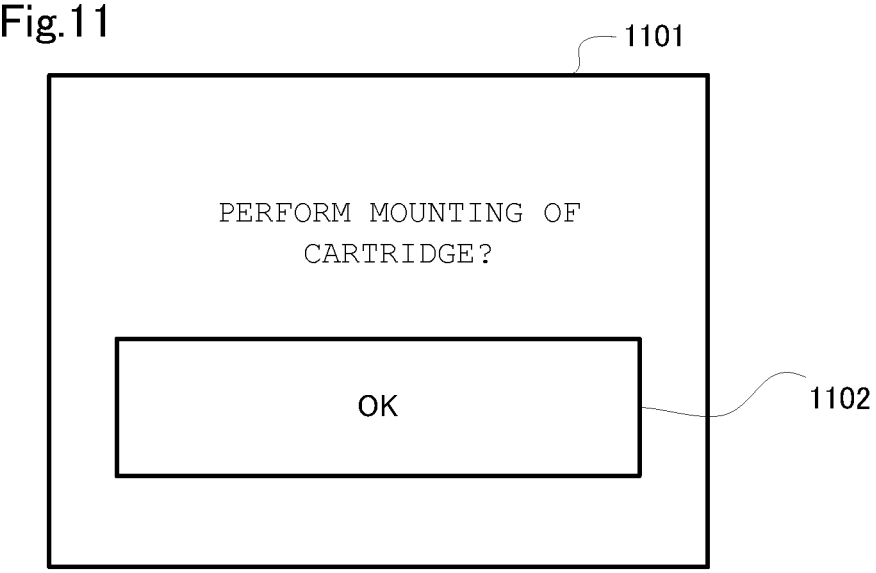
FIG. 11 is a diagram illustrating an example of a cartridge mounting request screen displayed on the display unit of the sterilization apparatus.

In addition, in step S102, in a case where it is determined that data could not be read from the RF-ID in step S101 (NO in step S102), and it is determined that a cartridge is not installed in the cartridge mounting location of the sterilization apparatus 100, the sterilization apparatus 100 displays a cartridge mounting request screen 1101 illustrated in FIG. 11 in step S116.

FIG. 11 is a diagram illustrating an example of the cartridge mounting request screen 1101 displayed on the display unit 102 of the sterilization apparatus 100.

An "OK" button 1102 is displayed on the cartridge mounting request screen 1101.

Further, the sterilization apparatus 100 determines whether the "OK" button 1102 on cartridge mounting request screen 1101 has been pressed by a user in step S117. In a case where the "OK" button 1102 has been pressed (YES in step S117), the cartridge mounting flap 101 is unlocked in step S118 and process returns to step S101. On the other hand in a case where the "OK" button 1102 has not been pressed (NO in step S117), display of the cartridge mounting request screen 1101 continues.

The processes of locking and unlocking the cartridge mounting flap 101 are performed according to the operation of the locking operation control unit 202.

Figure 5:
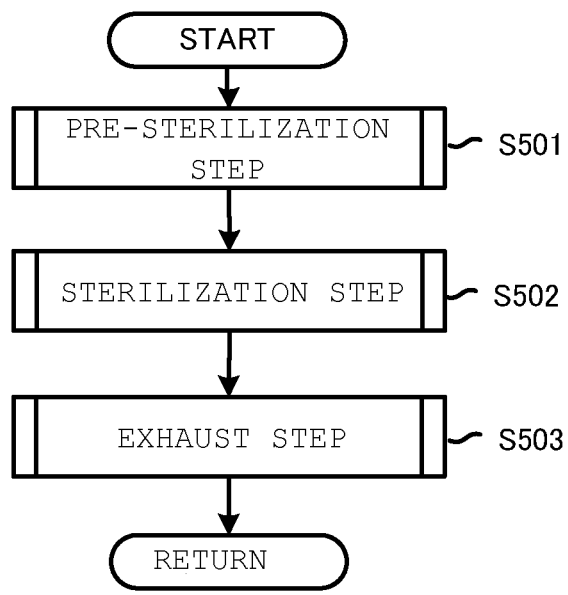
FIG. 5 is a diagram illustrating the processes of the sterilization process illustrated in step S111 of FIG. 4, in detail.

<Description of FIG. 5>

Next, with reference to FIG. 5, an example of the processes of the sterilization process illustrated in step S111 of FIG. 4B will be described in detail.

FIG. 5 is a diagram illustrating an example of the processes of the sterilization process illustrated in step S111 of FIG. 4B, in detail.

Each step (process) illustrated in FIG. 5 is performed by controlling the operation of each device in the sterilization apparatus using the computation processing unit 201 of the sterilization apparatus 100.

First, in step S501, the sterilization apparatus 100 operates the air transfer vacuum pump 220, suctions the gaseous matter of the sterilization chamber 219, and performs the processes of a pre-sterilization step until the air pressure in the sterilization chamber 219 is reduced to a predetermined air pressure (for example, 45 Pa). The processes of the pre-sterilization step will be described later in detail using FIG. 6.

Further, in step S502, the sterilization apparatus 100 inserts a sterilizing agent into the sterilization chamber 219 and performs a sterilization step that sterilizes target objects for sterilization. The processes of the sterilization step will be described later in detail using FIGS. 7A, 7B, 7C, and 7D.

Next, in step S503, the sterilization apparatus 100 performs the processes of a ventilation step for removing sterilizing agent contained in the sterilization chamber 219 and the vaporization furnace 216. The processes of the ventilation step will be described later in detail using FIG. 8.

Figure 6:
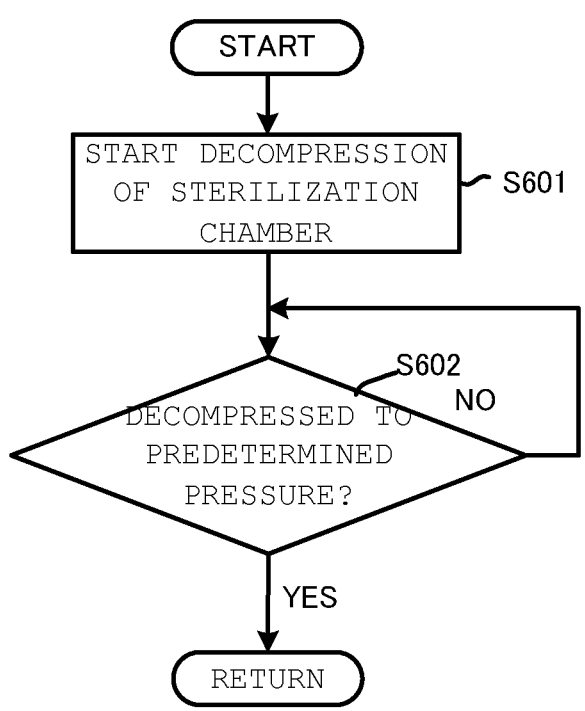
FIG. 6 is a diagram illustrating the processes of a pre-sterilization step illustrated in step S501 of FIG. 5, in detail.

<Description of FIG. 6>

Next, with reference to FIG. 6, an example of the processes of the pre-sterilization step illustrated in step S501 of FIG. 5 will be described in detail.

FIG. 6 is a diagram illustrating an example of the processes of the pre-sterilization step illustrated in step S501 of FIG. 5, in detail.

Each step (process) illustrated in FIG. 6 is performed by controlling the operation of each device in the sterilization apparatus using the computation processing unit 201 of the sterilization apparatus 100.

First, in step S601, the sterilization apparatus 100 operates the air transfer vacuum pump 220 and starts a process of suctioning the gaseous matter in the sterilization chamber 219.

Further, in step S602, the sterilization apparatus 100 determines whether the air pressure in the sterilization chamber 219 has been reduced to a predetermined air pressure (for example, 45 Pa). Specifically, it is determined whether the pressure air pressure in the sterilization chamber 219 measured by the pressure sensors provided in the sterilization chamber 219, has been reduced to a predetermined air pressure (for example, 45 Pa).

In step S602, in a case where it is determined that the air pressure in the sterilization chamber 219 has not been reduced to the predetermined air pressure (for example, 45 Pa) (NO in step S602), the operation of the air transfer vacuum pump 220 is continued, gaseous matter in the sterilization chamber 219 is suctioned and the air pressure in the sterilization chamber 219 is reduced.

On the other hand, in step S602, in a case where it is determined that the air pressure in the sterilization chamber 219 has been reduced to the predetermined air pressure (for example, 45 Pa) (YES in step S602), the operation of the air transfer vacuum pump 220 is continued, gaseous matter in the sterilization chamber 219 is suctioned and the process of step S502 is started.

Figure 7A:
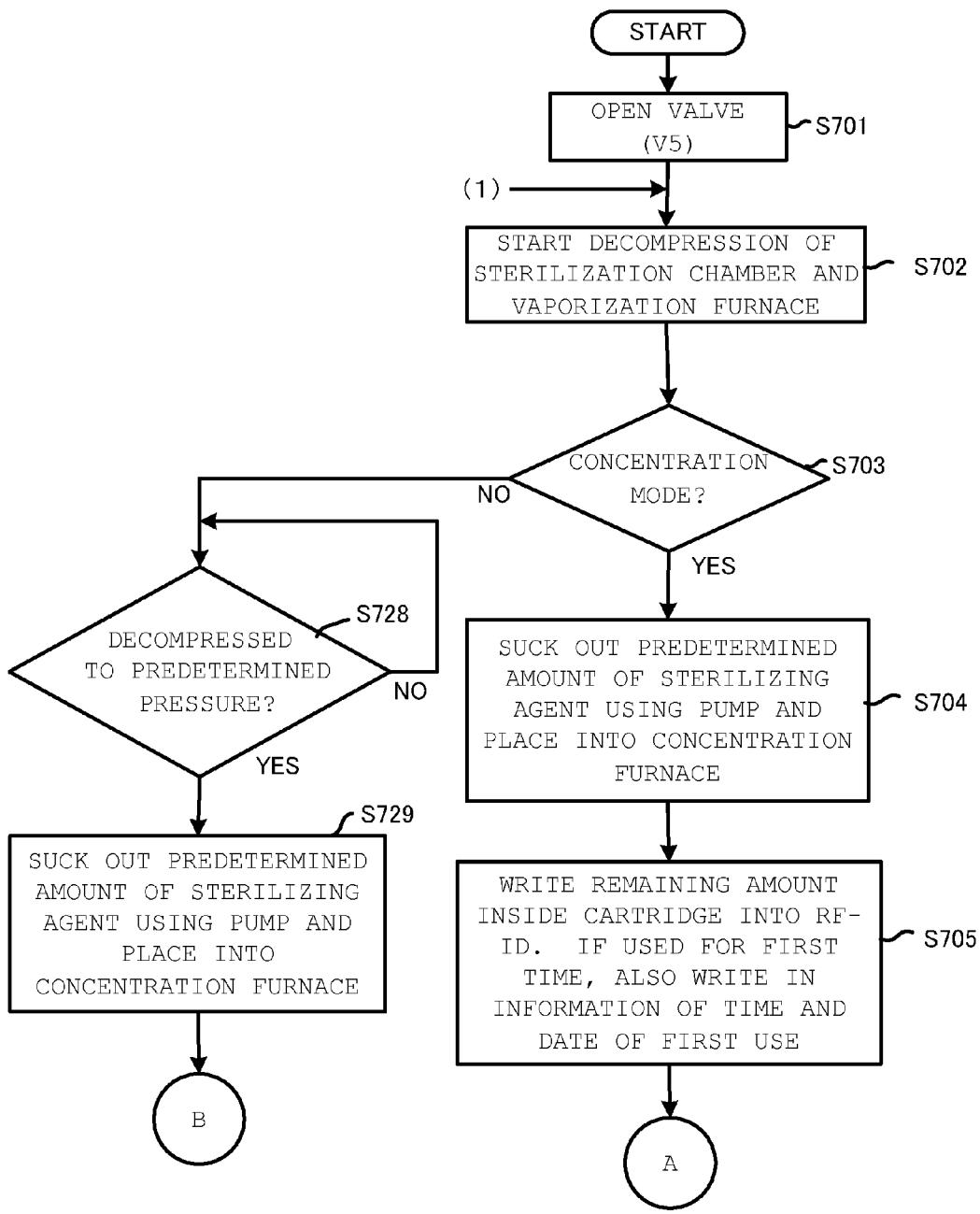
FIG. 7A, FIG. 7B, FIG. 7C, and FIG. 7D are diagrams illustrating the processes of the sterilization step illustrated in step S502 of FIG. 5, in detail.
Figure 7B:
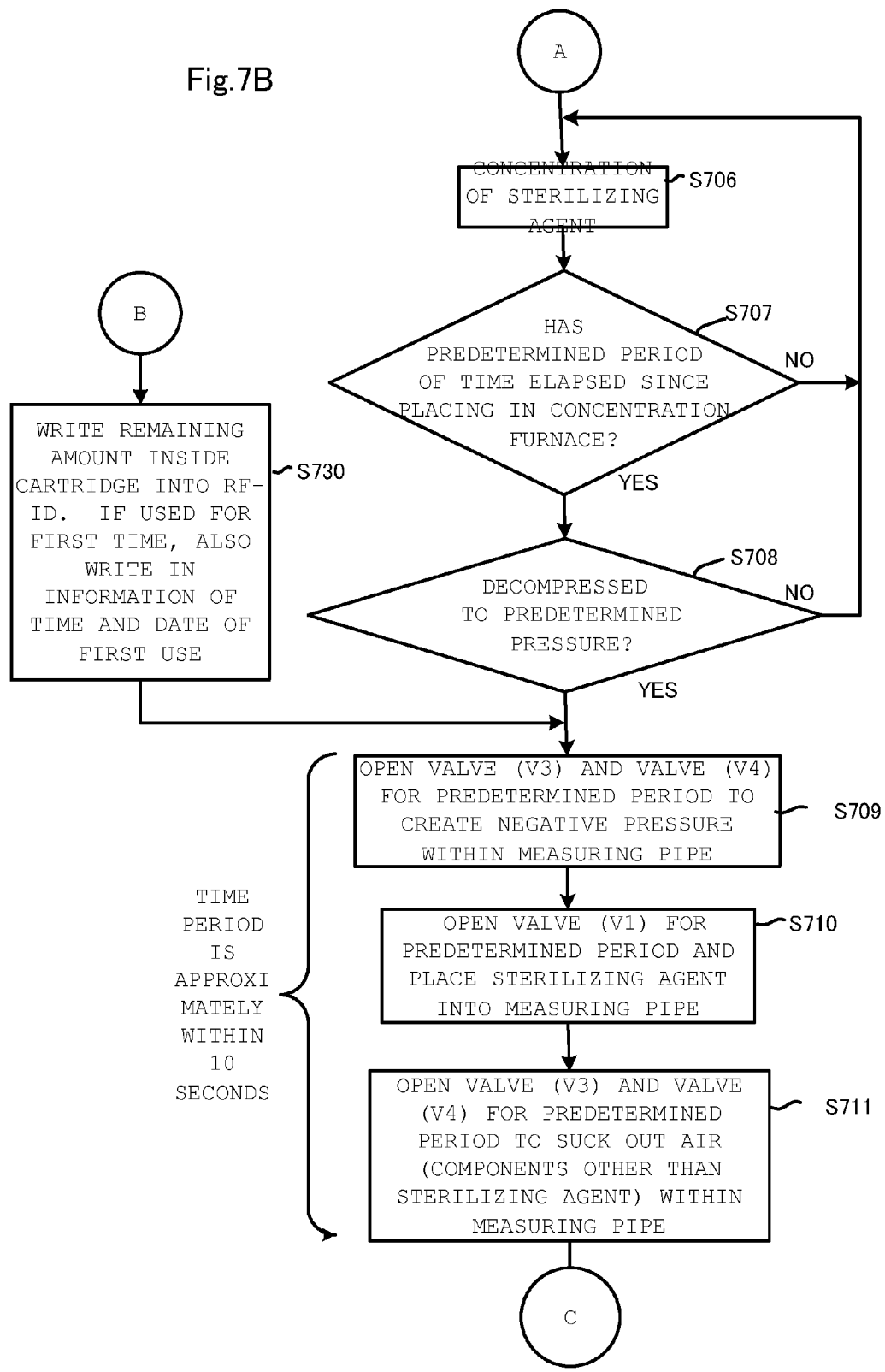
Figure 7C:
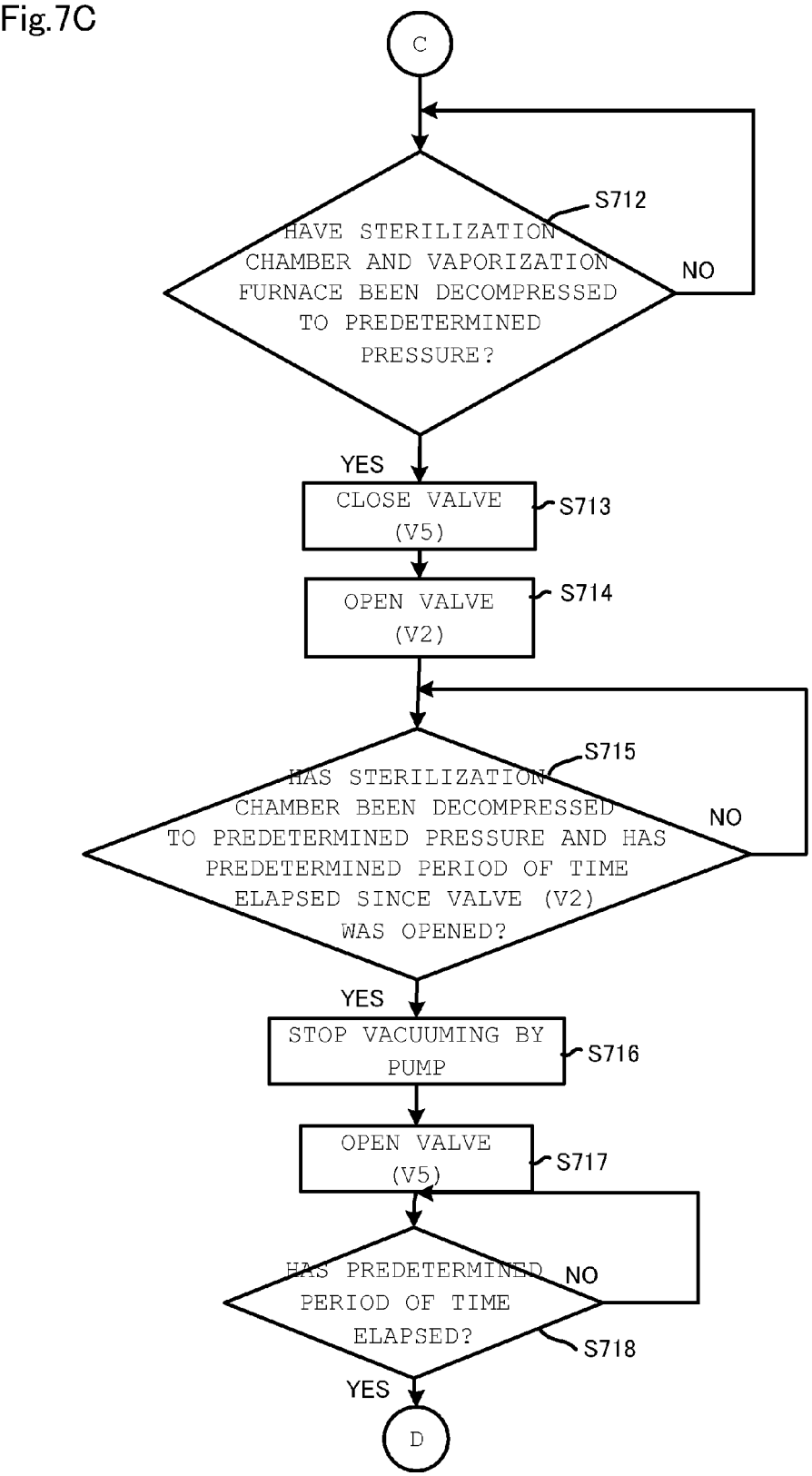
Figure 7D:
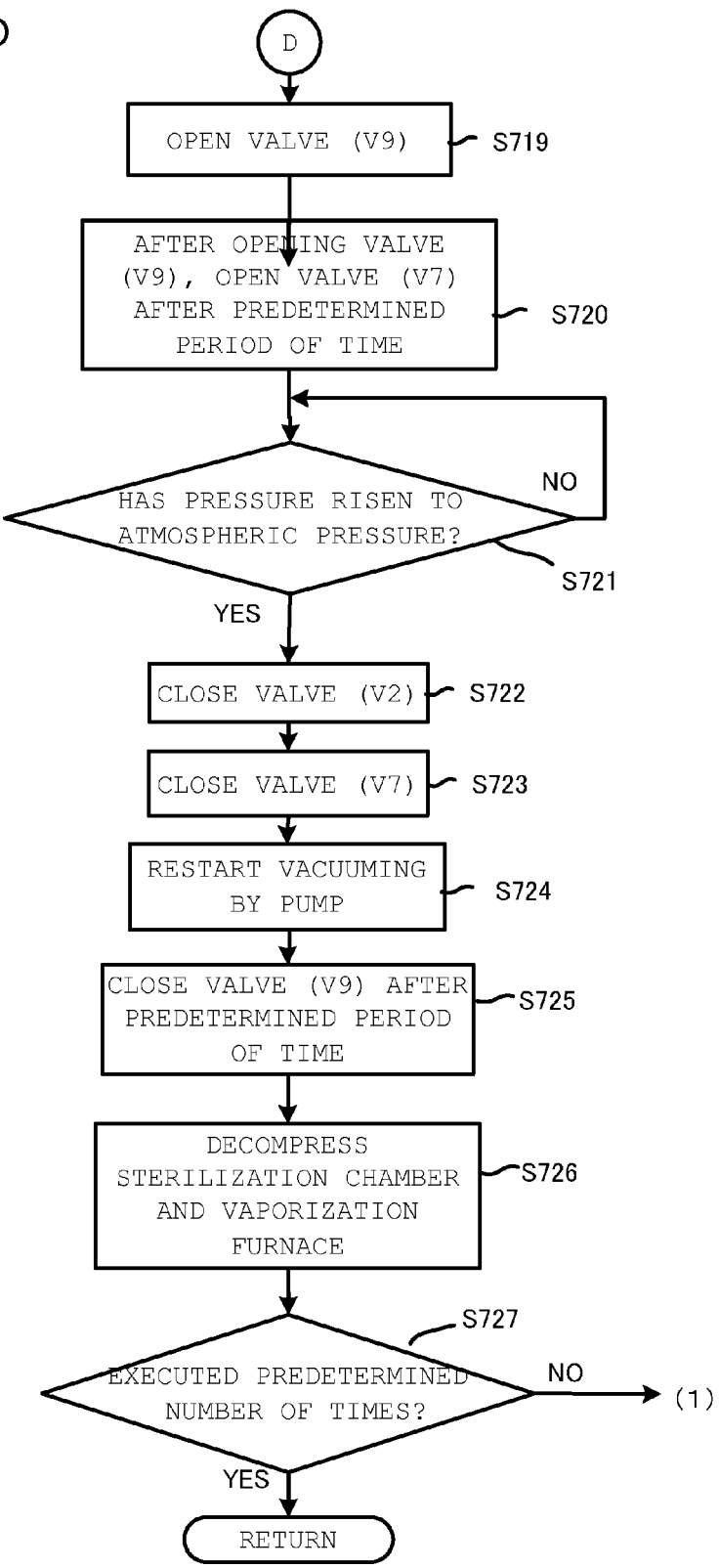

<Description of FIG. 7A, FIG. 7B, FIG. 7C, and FIG. 7C>

Next, using FIGS. 7A, 7B, 7C, and 7D, an example of the processes of the sterilization step illustrated in step S502 of FIG. 5 will be described in detail.

FIGS. 7A, 7B, 7C, and 7D are diagrams illustrating an example of the processes of the pre-sterilization step illustrated in step S502 of FIG. 5, in detail.

Each step (process) illustrated in FIGS. 7A, 7B, 7C, and 7D is performed by controlling the operation of each device in the sterilization apparatus using the computation processing unit 201 of the sterilization apparatus 100.

First, in step S701, the sterilization apparatus 100 opens the valve (V5) 217 to allow connection of the conduit pipe between the sterilization chamber 219 and the vaporization furnace 216. Thus, at this point, in step S702, since the gaseous matter in the sterilization chamber 219 is being suctioned and depressurized by the air transfer vacuum pump 220, depressurization in the sterilization chamber 219 and the vaporization furnace 216 is started.

Further, in step S703, the sterilization apparatus 100 determines whether the "Concentrate sterilizing agent and perform sterilization mode" button 304 or the "Perform sterilization without concentrating sterilizing agent mode" button 305 was pressed in step S110. In a case where it is determined that the "Concentrate sterilizing agent and perform sterilization mode" button 304 was pressed (YES in step S703), the process of step S704 is performed. In a case where it is determined that the "Perform sterilization without concentrating sterilizing agent mode" button 305 was pressed (NO in step S703), the process of step S728 is performed.

Firstly, a case where the "Concentrate sterilizing agent and perform sterilization mode" button 304 (a case where the sterilizing agent is concentrated and a sterilization process is performed) was pressed will be described.

In step S704, the sterilization apparatus 100, operates the rotary liquid transfer pump 207, and takes up a predetermined amount (for example, 2 ml) of the sterilizing agent in the cartridge 205. Further, the predetermined amount of sterilizing agent that was taken up is inserted into the concentration furnace 208. Here, the predetermined amount of sterilizing agent that is taken up is, for example, an amount that is capable of affecting a saturated state of the sterilizing agent in the space in the sterilization chamber 219.

Further, in step S705, the sterilization apparatus 100 writes the remaining amount of sterilizing agent in the cartridge 205 into the RF-ID of the cartridge 205 installed in the cartridge mounting location in the cartridge. Specifically, a value where the predetermined amount (for example, 2 ml) that was taken up of the cartridge 205 in step S704 has been subtracted from the remaining amount of sterilizing agent in the cartridge 205 that was read in step S101, is stored in the RF-ID.

In addition, in a case where information indicating date and time is not contained in the date and time of first use (the date and time at which the cartridge was first used in a sterilization apparatus) read from the RF-ID in step S101, it is determined that this time is the first use of the cartridge in a sterilization apparatus. Only in cases where it is determined that this time is the first use of a cartridge in a sterilization apparatus, current date and time information is also written to the RF-ID.

Next, in step S706, since the sterilization apparatus 100 constantly heats the heater provided in the concentration furnace 208 when the power of the sterilization apparatus 100 is on, the sterilizing agent inserted into the concentration furnace 208 in step S704 is heated by the heat of the heater and the moisture contained in the sterilizing agent in the concentration furnace 208 is evaporated.

The heater provided in the concentration furnace 208 is constantly heated when the power of the sterilization apparatus 100 is on so that it is possible to use the sterilization apparatus immediately at any time in an operating room or the like. Thus, by eliminating the time it takes to heat the heater of the concentration furnace, it is possible to use the sterilization apparatus immediately at any time.

In other words, in a case where the sterilizing agent is hydrogen peroxide (also referred to as aqueous solution of hydrogen peroxide), the heater provided in the concentration furnace 208 is specifically, for example, warmed to 80° C. Thus, it is possible to mainly evaporate (vaporize) moisture and concentrate the sterilizing agent.

Next, in step S707, the sterilization apparatus 100 determines whether a predetermined period of time (for example, 6 minutes) has passed since the sterilizing agent was inserted into the concentration furnace 208 in step S704. Further, when it is determined that the predetermined period of time has passed since the sterilizing agent was inserted into the concentration furnace 208 (YES in step S707), the process of step S708 is performed. On the other hand, in a case where it is determined that a predetermined period of time has not passed since the sterilizing agent was inserted into the concentration furnace 208 (NO in step S707), the sterilizing agent is left in the concentration furnace 208 and concentration of the sterilizing agent is continued.

Further, in step S708, the sterilization apparatus 100 determines whether the air pressure in the sterilization chamber 219 and the vaporization furnace 216 has been reduced to a predetermined air pressure (for example, 500 Pa).

Further, in a case where the air pressure in the sterilization chamber 219 and the vaporization furnace 216 has been reduced to the predetermined air pressure (YES in step S708), in step S709, by opening the valve (V3) 212 and the valve (V4) 213 for a predetermined period of time (opening the valve (V3) 212 and the valve (V4) 213 for a predetermined period of time (for example 3, seconds) and then closing the valve (V3) 212 and the valve (V4) 213), the sterilization apparatus 100 depressurizes the measuring pipe 214. On the other hand, in a case where the air pressure in the sterilization chamber 219 and the vaporization furnace 216 have not been reduced to the predetermined air pressure (NO in step S708), concentration of the sterilizing agent is continued. That is, in the case where the concentrated mode, the sterilizing agent in the concentration furnace is inserted into the measuring pipe 214 at the third timing of the air pressure in the sterilization chamber 219 and the vaporization furnace 216 has been reduced to the predetermined air pressure.

Further, next, in step S710, when the sterilization apparatus 100 opens the valve (V1) for a predetermined period of time (for example, 3 seconds) after opening the valve (V3) 212 and the valve (V4) 213 for a predetermined period of time and then closing the valve (V3) 212 and the valve (V4) 213 in step S709, since the air pressure in the measuring pipe 214 is lower than air pressure in the concentration furnace 208 (external), the sterilizing agent in the concentration furnace 208 is drawn into the measuring pipe 214. Here by opening the valve (V1) for a predetermined period of time and then closing the valve (V1), the sterilizing agent in the concentration furnace 208 is drawn into the measuring pipe 214. Here, not only the sterilizing agent, but also the air in the concentration furnace 208 is drawn into the measuring pipe 214.

Further, even after this, the air transfer vacuum pump 220 continues depressurization of the sterilization chamber 219.

Therefore, the air pressure in the sterilization chamber 219 is lower than the air pressure in the measuring pipe. Specifically, the air pressure in the sterilization chamber 219 is approximately 400 Pa and the air pressure in the measuring pipe is a value that is approximately atmospheric pressure (101325 Pa). Since the air in the concentration furnace 208 is drawn into the measuring pipe 214 along with the sterilizing agent, the air pressure in the measuring pipe rises to almost atmospheric pressure.

Next, in step S711, the sterilization apparatus 100 opens the valve (V3) 212 and the valve (V4) 213 for a predetermined period of time (for example, 3 seconds) and the air (liquid sterilizing agent not included) in the measuring pipe is expelled into the sterilization chamber 219. More specifically, here, the valve (V3) 212 and the valve (V4) 213 are opened and once the predetermined period of time has passed, the valve (V3) 212 and the valve (V4) 213 are closed.

Next, the sterilization apparatus 100, in step S712, determines whether the air pressure in the sterilization chamber 219 and the vaporization furnace 216 has been depressurized to a predetermined air pressure (for example, 80 Pa) and in a case where it is determined that the air pressure has been reduced, the valve (V5) 217 is closed in step S713.

Further, in step S714, the sterilization apparatus 100 opens the valve (V2) 215. Thus, the sterilizing agent in the measuring pipe 214 is drawn into the vaporization furnace 216, and is gasified in the vaporization furnace 216.

Here, the sterilizing agent is gasified in the vaporization furnace as molecular clusters.

The volume of the sterilization chamber is greater than that of the vaporization furnace, and thus, in the vaporization furnace, the sterilizing agent is gasified as molecular clusters. The reason for this is that, since the volume of the vaporization furnace is less than that of the sterilization chamber, the distance between molecules of the sterilizing agent in the sterilization chamber is small and there is a tendency for molecular clusters to form as a result of intermolecular forces.

At this time, the air transfer vacuum pump 220 still continues suctioning of gaseous matter in the sterilization chamber 219 and the air pressure in sterilization chamber 219 is reduced. The air pressure inside the vaporization furnace 216 into which the sterilizing agent in the measuring pipe 214 was drawn, rises.

In other words, the air pressure in the vaporization furnace 216 is higher than the air pressure in the sterilization chamber 219.

Next, in step S715, sterilization apparatus 100 determines whether the air pressure in the sterilization chamber 219 has been reduced to a predetermined air pressure (for example, 50 Pa) and whether the predetermined period of time has passed since the valve (V2) 215 was opened in step S714. In a case where the air pressure in the sterilization chamber 219 has been reduced to a predetermined air pressure (for example, 50 Pa) and the predetermined period of time has passed since the valve (V2) 215 was opened in step S714 (YES in step S715), the suctioning (vacuuming) of the sterilization chamber 219 using the air transfer vacuum pump 220 is stopped in step S716 and the valve (V5) 217 is opened in step S717. Thus, the sterilizing agent which vaporized in the sterilization chamber 219 is to diffuse and it becomes possible to sterilize target objects for sterilization.

The sterilizing agent diffuses since the air pressure in the sterilization chamber 219 (for example, 50 Pa) is lower than the air pressure in the vaporization furnace 216.

Here, since it is possible to further subdivide the molecular clusters of the vaporization furnace and cause the sterilization agent to diffuse in the sterilization chamber to a greater extent, it is possible to improve the sterilizing action of the sterilizing agent that is diffused.

In addition, it is possible to effectively sterilize fine cavities such as those of target objects for sterilization.

Further, it is determined whether a predetermined period of time (for example, 330 seconds) has passed since the valve (V5) 217 was opened in step S717 and when it is determined that the predetermined period of time (for example 330 seconds) has passed since the valve (V5) 217 was opened (YES in step S718), the valve (V9) 227 is opened in step S719.

Thus, since the air pressure in the vaporization furnace 216 and the sterilization chamber 219 is lower than the air pressure outside the sterilization apparatus 100, external air (air) from outside the sterilization apparatus 100, which has been cleaned by the intake HEPA filter, is drawn into the vaporization furnace 216. Further, sterilization agent in the vaporization furnace 216 that has been filled with gaseous matter and sterilizing agent that has adhered to the inner surfaces of the vaporization furnace 216, are fed into the sterilization chamber 219 by the air fed into the vaporization furnace 216, and the sterilizing action on the target objects for sterilization in the sterilization chamber 219 heightens. In other words, for example, the sterilizing action on portions which are difficult to sterilize such as the insides of thin tubes of target objects heightens.

Further, when a predetermined period of time (15 seconds) since the valve (V9) 227 was opened in step S719 has passed, the sterilization apparatus 100, opens the valve (V7) 226, and the external air from outside the sterilization apparatus 100, which has been cleaned by the intake HEPA filter 210, is drawn into the sterilization chamber 219. The reason for this is that, since the air pressure in the sterilization chamber 219 and the vaporization furnace 216 is lower than the air pressure outside the sterilization apparatus 100, the external air outside the sterilization apparatus 100 is drawn into the sterilization chamber 219.

As a result of this, the sterilizing action on portions which are difficult to sterilize (particularly cavity portions) such as the insides of thin tubes of target objects for sterilization heightens.

Next, the sterilization apparatus 100 determines whether the vaporization furnace 216 and the sterilization chamber 219 have risen to atmospheric pressure. In a case where it is determined that they have risen to atmospheric pressure (YES in step S721), the valve (V2) 215 is closed in step S722.

Next, the sterilization apparatus 100 closes the valve (V7) 226 in step S723 and restarts the suctioning (vacuuming) of the sterilization chamber 219 using the air transfer vacuum pump 220 in step S724. As a result, external air from outside the sterilization apparatus 100, which has been cleaned by the intake HEPA filter 210, is drawn into the vaporization furnace 216 through the conduit pipe between the vaporization furnace 216 and the intake HEPA filter 210. Further, sterilization agent in the vaporization furnace 216 that has been filled with gaseous matter, and sterilizing agent that has adhered to the inner surfaces of the vaporization furnace 216, are further fed into the sterilization chamber 219 by the air fed into the vaporization furnace 216.

As a result, in addition to increasing the sterilizing action on portions which are difficult to sterilize (particularly cavity portions) such as the insides of thin tubes of target objects, it is possible to effectively reduce the sterilizing agent in the vaporization furnace 216.

Further, in step S725, after a predetermined period of time (for example 15 seconds) has elapsed since the suctioning (vacuuming) of the sterilization chamber 219 using the air transfer vacuum pump 220 is resumed in step S724, the sterilization apparatus 100 closes the valve (V9) 227.

At this time, in step S726, the air transfer vacuum pump 220 still continues suctioning (vacuuming) of the sterilization chamber 219. The sterilization chamber 219 and the vaporization furnace 216 are sealed as a result of step S725, and the sterilization chamber 219 and the vaporization furnace 216 are depressurized.

Next, in step S727, the sterilization apparatus 100 determines whether the processes from steps S702 to S726 have been executed a predetermined number of times (for example 4. times). In a case where it is determined that the processes have been executed the predetermined number of times (YES in step S727), the process of step S503 is performed. On the other hand, in a case where it is determined that the processes from steps S702 to S726 have not been executed the predetermined number of times, the processes from step S702 onwards are performed again. In this way, since the processes from steps S702 to S726 are executed a predetermined number of times, the effect of the sterilizing action on the target objects increases and it is possible to sterilize the target objects sufficiently.

Next, in a case where it has been determined that the "Perform sterilization without concentrating sterilizing agent mode" button 305 was pressed in step S703 (i.e., a case of performing sterilization without concentrating the sterilizing agent) will be described.

In a case where it is determined that the "Perform sterilization without concentrating sterilizing agent mode" button 305 was pressed (NO in step S703), the sterilization apparatus 100 determines whether the air pressure in the sterilization chamber 219 and the vaporization furnace 216 has been reduced to a predetermined air pressure (for example, 1000 Pa) in step S728.

Further, in a case where it is determined that the air pressure in the sterilization chamber 219 and the vaporization furnace 216 has been reduced to the predetermined air pressure (for example, 100 Pa) (YES in step S728), the sterilization apparatus 100 operates the rotary liquid transfer pump 207 and takes up a predetermined amount (for example, 2 ml) of the sterilizing agent in the cartridge 205. Further, the predetermined amount of sterilizing agent that was taken up is inserted into the concentration furnace 208 in step S729. In this way, according to whether the concentrated mode is used, the timing at which the sterilizing agent in the cartridge 205 is taken up and the timing at which the sterilizing agent is inserted into the concentration furnace 208 are differentiated. As a result, it is possible to switch between a sterilization process using a concentrated sterilizing agent and a sterilization process using a sterilizing agent that has not been concentrated. That is, in the case where the concentrated mode, the sterilization apparatus 100 is operable to control the transfer of the sterilizing agent to the concentration furnace 208 at the first timing (in step S704). In the case where the non-concentrated mode, the sterilization apparatus 100 is operable to control the transfer of the sterilizing agent to the concentration furnace 208 at the second timing (in step S729). The first timing is a timing later than the second timing.

Here, the predetermined amount of sterilizing agent that is taken up is, for example, an amount that can achieve a saturated state of the sterilizing agent in the space in the sterilization chamber 219.

Next, in step S730, the sterilization apparatus 100 writes the remaining amount of sterilizing agent in the cartridge 205 into the RF-ID of the cartridge 205 installed in the cartridge mounting location. Specifically, a value where the predetermined amount (for example, 2 ml) that was taken up from the cartridge 205 in step S729 has been subtracted from the remaining amount of sterilizing agent in the cartridge 205 that is read in step S101, is stored in the RF-ID.

In addition, in a case where information indicating date and time is not contained in the date and time of first use (the date and time at which the cartridge was first used in a sterilization apparatus) read from the RF-ID in step S101, it is determined that this time the cartridge is first used in a sterilization apparatus. Only in that case where it is determined that this time a cartridge is first used in a sterilization apparatus, current date and time information is written into the RF-ID.

Further, when the sterilization apparatus 100 performs the process of step S730, the processes from step S709 and thereafter are performed, which have already been described.

In step S728, if the air pressure in the sterilization chamber 219 becomes a predetermined air pressure (for example, 1000 Pa), since taking-up of the sterilizing agent is started in step S729 and the air pressure drops below 500 Pa when taking-up of the sterilizing agent is finished in step S729, it is possible to proceed to step S709 efficiently. That is, in the case where the non-concentrated mode, the sterilizing agent in the concentration furnace is inserted into the measuring pipe 214 at the forth timing of taking-up of the sterilizing agent is finished in step S729. the third timing is different from the fourth timing.

In this way, after the air pressure in the sterilization chamber 219 and the vaporization furnace 216 has been reduced to the predetermined air pressure (for example, 1000 Pa) that starts depressurization in the measuring pipe, the predetermined amount of sterilizing agent that was taken up is inserted into the concentration furnace 208. Immediately after that it is possible to depressurize the measuring pipe 214 in step S709 After that, since the sterilizing agent in the concentration furnace is inserted into the measuring pipe in step S710, it is possible to insert the sterilizing agent into the measuring pipe 214 immediately. In other words, it is possible to insert the sterilizing agent into the measuring pipe 214 without concentrating in the concentration furnace 208.

Figure 8:
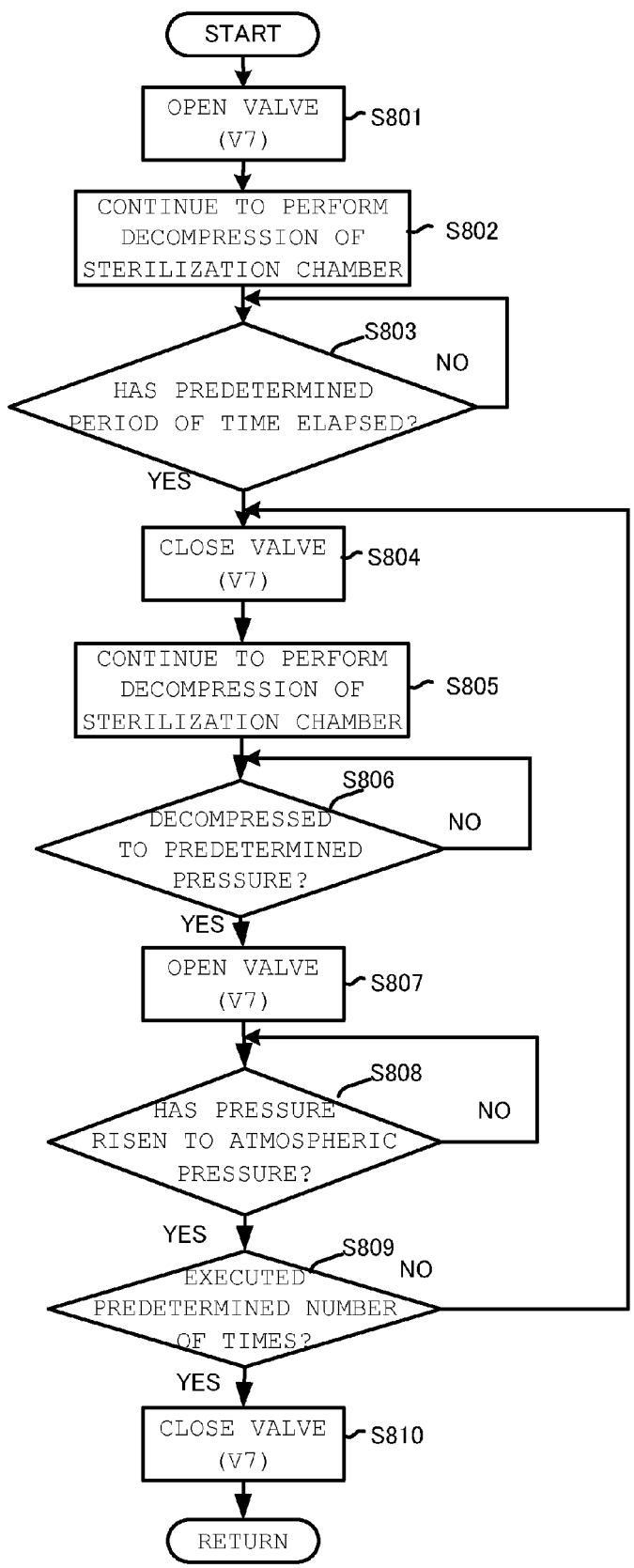
FIG. 8 is a diagram illustrating the processes of the ventilation step illustrated in step S503 of FIG. 5, in detail.

<Description of FIG. 8>

Next, using FIG. 8, an example of the processes of the ventilation step illustrated in step S503 of FIG. 5 will be described in detail.

FIG. 8 is a diagram illustrating an example of the processes of the ventilation step illustrated in step S503 of FIG. 5, in detail.

Each step (process) illustrated in FIG. 8 is performed by controlling the operation of each device in the sterilization apparatus using the computation processing unit 201 of the sterilization apparatus 100.

First, in step S801, the sterilization apparatus 100 opens the valve (V7) 226.

Further, in step S802, the sterilization apparatus 100 performs suction (vacuum) in the sterilization chamber 219 using the air transfer vacuum pump 220.

After opening the valve (V7) 226 in step S801, suction (vacuum) is performed in the sterilization chamber 219 using the air transfer vacuum pump 220 in step S802. After a predetermined period of time has elapsed (YES in step S803), the valve (V7) 226 closes in step S804, and the air transfer vacuum pump 220 continues performing suction (vacuum) in the sterilization chamber 219. Thereby, the pressure is reduced in the sterilization chamber 219.

Further, the sterilization apparatus 100 opens the valve (V7) 226 in step S807 when the pressure in the sterilization chamber 219 is reduced to a predetermined air pressure (50 Pa) (YES in step S806). As a consequence, the air outside the sterilization apparatus 100 that has been cleaned using the intake HEPA filter 210 is drawn into the sterilization chamber 219. Because air pressure in the sterilization chamber 219 is lower than air pressure outside the sterilization apparatus 100, the air outside the sterilization apparatus 100 is drawn into the sterilization chamber 219.

Next, the sterilization apparatus 100, determines if the air pressure in the sterilization chamber 219 was raised up to the atmospheric pressure. In a case where the air pressure in the sterilization chamber 219 is raised up to the atmospheric pressure (YES in step S808), it is determined if the process from steps S804 to S808 has been performed a predetermined number of times (for example, 4 times) in step S809. In a case where the process from steps S804 to S808 has been performed a predetermined number of times (YES in step S809), the valve (V7) 226 is closed in step S810 to terminate ventilation step.

On the other hand, in a case where the process from steps S804 to S808 has not been performed a predetermined number of times (NO in step S809), the process is repeated from step S804.

In so doing, sterilizing agent that has adhered to the inner surfaces of the sterilization chamber 219 and sterilizing agent remaining as gaseous matter in the sterilization chamber 219 are suctioned by the air transfer vacuum pump 220. Here, the suctioned gaseous matter (including the sterilizing agent) passes through the exhaust HEPA filter 221, the sterilizing agent is decomposed in sterilizing agent decomposition apparatus 222 and the molecules are released to the outside after decomposition.

Figure 9:
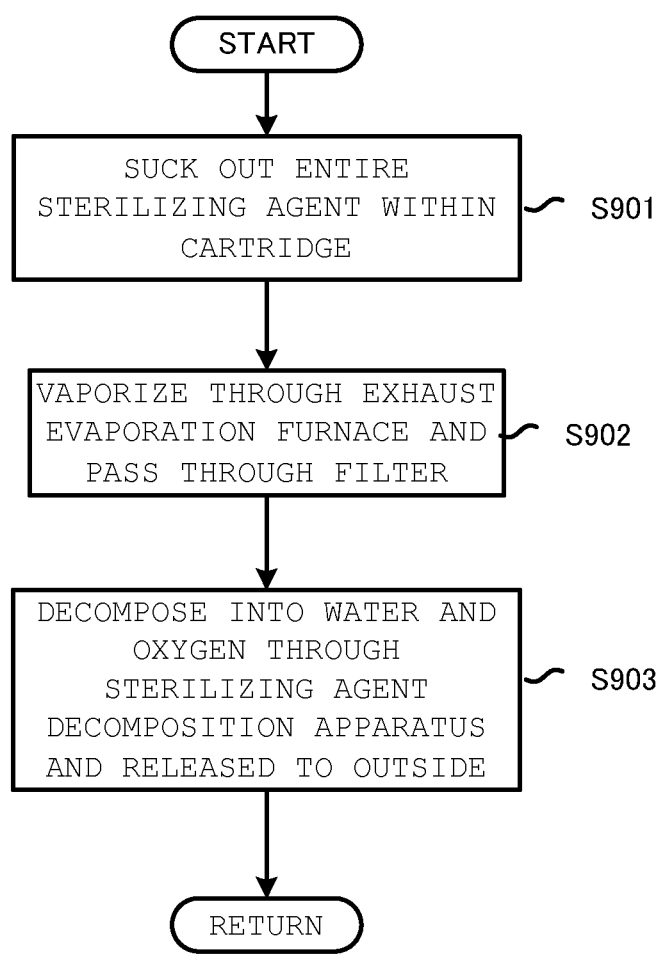
FIG. 9 is a diagram illustrating the processes of the sterilization discharge process illustrated in step S114 of FIG. 4B, in detail.

<Description of FIG. 9>

Next, using FIG. 9, an example of the sterilization discharge process illustrated in step S114 of FIG. 4B will be described in detail.

FIG. 9 is a diagram illustrating an example of the sterilization discharge process illustrated in step S114 of FIG. 4B in detail.

Each step (process) illustrated in FIG. 9 is performed by controlling the operation of each device in the sterilization apparatus using the computation processing unit 201 of the sterilization apparatus 100.

First, in step S901, the sterilization apparatus 100, using the rotary liquid transfer pump 223, suctions all the liquid sterilizing agent in the cartridge 205, and all of the sterilizing agent which is sent through the conduit pipe between the liquid sensor 204 and the rotary liquid transfer pump 223 is sent into the exhaust evaporation furnace 224 through the conduit pipe between the rotary liquid transfer pump 223 and the exhaust evaporation furnace 224.

Next, in step S902, the sterilization apparatus 100, using the exhaust evaporation furnace 224, heats all of the liquid sterilizing agent (sterilizing agent which is accumulated in the exhaust evaporation furnace 224) which is transferred through the conduit pipe between the rotary liquid transfer pump 223 and the exhaust evaporation furnace 224. The sterilization apparatus 100 heats the sterilizing agent, using a heater which the exhaust evaporation furnace 224 is equipped with, and all of the sterilizing agent is gasified. Next, the gasified sterilizing agent is transferred to the exhaust HEPA filter 221 through the conduit pipe between the exhaust evaporation furnace 224 and the exhaust HEPA filter 221.

Here, the heater which the exhaust evaporation furnace 224 is equipped with is heated, for example, to a temperature higher than the boiling point of the sterilizing agent (hydrogen peroxide; boiling point of hydrogen peroxide is 141 degrees C.). Therefore, the sterilizing agent will be completely gasified by exhaust evaporation furnace 224.

Further, using the exhaust HEPA filter 221, the sterilization apparatus 100 cleans the gasified sterilizing agent which is transferred along the conduit pipe between exhaust evaporation furnace 224 and the exhaust HEPA filter 221, and the cleaned gaseous matter (including sterilizing agent) is transferred to the sterilizing agent decomposition apparatus 222 through the conduit pipe between the sterilizing agent decomposition apparatus 222 and the exhaust HEPA filter 221.

Further, in step S903, the sterilizing agent decomposition apparatus 222 decomposes the molecules of the sterilizing agent which are included in the gaseous matter that is transferred from the conduit pipe between the sterilizing agent decomposition apparatus 222 and the exhaust HEPA filter 221, and releases the molecules which are generated by decomposition to the outside of the sterilization apparatus 100.

Figure 10:
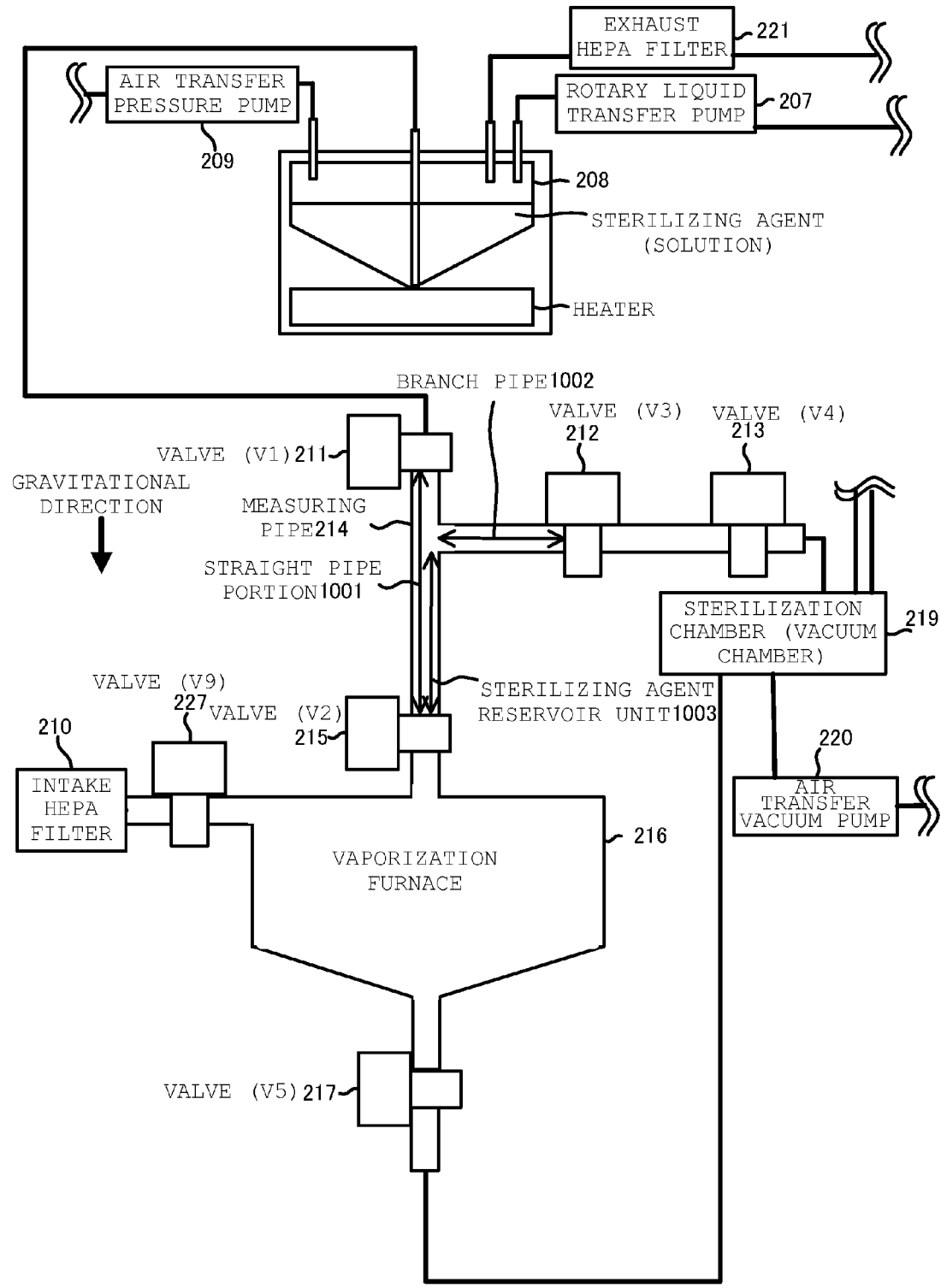
FIG. 10 is a diagram illustrating a configuration block diagram for the hardware configuration of a concentration furnace, a valve (V1), a valve (V3), a valve (V4), a measuring pipe, a valve (V2), a vaporization furnace, a valve (V5) and a valve (V9) of the sterilization apparatus according to an embodiment of the invention.

<Description of FIG. 10>

Further, using FIG. 10, a block configuration according to the hardware configuration of the concentration furnace 208, the valve (V1) 211, the valve (V3) 212, the valve (V4) 213, the measuring pipe 214, the valve (V2) 215, the vaporization furnace 216, the valve (V5) 217, and the valve (V9) 227 of the sterilization apparatus 100 according to an embodiment of the present invention will be described.

FIG. 10 is a diagram illustrating an example of a configuration block diagram according to the hardware configuration of a concentration furnace 208, a valve (V1) 211, a valve (V3) 212, a valve (V4) 213, a measuring pipe 214, a valve (V2) 215, a vaporization furnace 216, a valve (V5) 217 and a valve (V9) 227 of the sterilization apparatus 100 according to an embodiment of the present invention.

The hardware in FIG. 10, if it is the same hardware as illustrated in FIG. 2, is denoted by the same reference numerals.

In steps S704 and S729, the rotary liquid transfer pump 207 is operated such that a predetermined amount (for example, 2 ml) of the sterilizing agent in the cartridge 205 is sucked out, and the predetermined amount of sucked out sterilizing agent is fed into the concentration furnace 208.

In step S706, the concentration furnace 208, as illustrated in FIG. 10, is provided with a heater at the lower portion of the concentration furnace 208, and the sterilizing agent is heated by this heater. In a case where the sterilizing agent is a solution of hydrogen peroxide, the water is gasified by the heater. Further, the gasified water is forced into the conduit pipe that leads to the exhaust HEPA filter 221 by the air fed through the conduit pipe from the air transfer pressure pump 209, and exhausted from the concentration furnace 208. In so doing, sterilizing agent (aqueous solution of hydrogen peroxide) is concentrated.

As described in FIG. 7B, in step S710, the sterilizing agent in the concentration furnace 208 enters into the measuring pipe 214.

The measuring pipe 214, as illustrated in FIG. 10, includes a straight pipe section 1001 and a branch pipe section 1002.

The straight pipe section 1001 is a portion of the straight tube. The piping of straight pipe section 1001 is disposed in the gravitational direction.

In addition, the branch pipe section 1002 is a pipe-like portion which extends branch-like from the intermediate or upper sections of the straight pipe section 1001.

The straight pipe section 1001 is installed to be orthogonal to the axial center of the straight pipe section and the axial center of the branch pipe section 1002.

In order to make such a configuration, the straight pipe section 1001 in the measuring pipe 214 is configured so that the sterilizing agent entering from the concentration furnace 208 accumulates therein. The portion of the straight pipe section 1001 where sterilizing agent accumulates is referred to as a sterilizing agent reservoir 1003.

In other words, the sterilizing agent entering from the concentration furnace 208 has sufficient space to enter the sterilizing agent reservoir 1003.

Therefore, the sterilizing agent entering from the concentration furnace 208 accumulates in the sterilizing agent reservoir 1003, and the sterilizing agent together with the air entering from the concentration furnace 208 permeates the space other than the space of the sterilizing agent that has accumulated in sterilizing agent reservoir 1003. More specifically, since space other than the space of sterilizing agent is in communication with the space in the branch pipe section 1002 in the branch pipe section 1002, the air is sucked into the sterilization chamber 219 by opening the valve (V3) 212 and the valve (V4) 213 in step S711.

Further, by opening the valve (V2) in step S714, the sterilizing agent that accumulates in sterilizing agent reservoir 1003 is drawn into the vaporization furnace 216 and vaporizes. As illustrated in FIG. 10, the sterilizing agent is easily gasified by the liquid sterilizing agent entering the vaporization furnace 216 from the upper portion of the vaporization furnace 216.

Further, as illustrated in FIG. 10, the conduit pipe between the intake HEPA filter 210 and the vaporization furnace 216 is provided in the upper portion of the vaporization furnace 216. Therefore, when the valve (V9) opens in step S719, because air is removed from the upper portion of the vaporization furnace 216 toward the sterilization chamber 219 at the bottom of the vaporization furnace 216, the sterilizing agent that attaches to the inside of the vaporization furnace 216 and the sterilizing agent that was gasified in the vaporization furnace 216 are easier to remove across a wide range, and it is possible that more of the removed sterilizing agent flows into the sterilization chamber 219.

As above described, according to the present invention, since the timing at which the sterilizing agent in the cartridge is sucked out changes between the concentrated mode (304 in FIG. 3) and the non-concentrated mode (305 in FIG. 3), it is possible to provide a sterilization apparatus in which the sterilization process using a concentrated sterilizing agent and the sterilization process using a sterilizing agent which has not been concentrated can be switched without changing the transport path of the sterilizing agent.

Water molecules which have a lighter mass than hydrogen peroxide molecules move faster in the sterilization chamber. Further, in a case where the sterilizing agent is concentrated, and in a case where it is not concentrated, the amount of molecules entering in the cavity portions of the tube of the object for sterilization in the sterilization chamber is substantially unchanged. Therefore, in a case where the sterilizing agent is concentrated, since the moisture contained in the aqueous solution of hydrogen peroxide is reduced due to concentration of the aqueous solution of hydrogen peroxide, (for example, the amount of water molecules that reach the cavity portions of the tube of the object for sterilization in the sterilization chamber is reduced) it is possible to increase an amount of hydrogen peroxide molecules entering the cavity portions. As a result, by concentrating the sterilizing agent, it is possible to enhance the effect of sterilization in the cavity portion.

While the present invention has been described with reference to particular embodiments, it is to be understood that the invention is not limited to the disclosed embodiments.

This application claims priority from Japanese Patent Application No. 2011-222383 filed Oct. 6, 2011, which is hereby incorporated by reference herein in its entirety.

What is claimed is:

1. A sterilization apparatus for sterilizing target objects using a sterilizing agent which is transferred to a sterilization chamber after transferring to a concentration chamber, comprising:
    transfer means for transferring, from a container filled with a liquid sterilizing agent, the liquid sterilizing agent to the concentration chamber;
    the concentration chamber for concentrating the liquid sterilizing agent transferred by the transfer means by applying heat to the transferred liquid sterilizing agent;
    the sterilization chamber for sterilizing the target objects using sterilizing gas obtained by vaporizing the liquid sterilizing agent which has been concentrated by being heated by the concentration chamber without using gas generated as a result of vaporization performed by the heating by the concentration chamber; and
    receiving means for receiving, from a user via an operation unit, selection of one mode from among a highly-concentrated mode in which sterilization by using a liquid sterilizing agent highly concentrated in the concentration chamber is performed and a low-concentrated mode in which sterilization by using a liquid sterilizing agent not highly concentrated in the concentration chamber is performed, wherein
    the liquid sterilizing agent transferred to the concentration chamber by the transfer means is heated by the concentration chamber during a period longer in a case where the selection of the highly-concentrated mode is received by the receiving means than in a case where the selection of the low-concentrated mode is received by the receiving means.

2. A sterilization apparatus according to claim 1,
wherein the transfer means, in the case where the selection of the low-concentrated mode is received by the receiving means, transfers the liquid sterilizing agent to the concentration chamber if a first predetermined condition for transferring the liquid sterilizing agent to the concentration chamber is satisfied.

3. A sterilization apparatus according to claim 2,
wherein, in a case where the selection of the highly-concentrated mode is received by the receiving means, the transfer means transfers the liquid sterilizing agent to the concentration chamber, regardless of whether or not the first predetermined condition is satisfied.

4. A sterilization apparatus according to claim 2,
wherein the first predetermined condition includes a condition that indicates whether the sterilization chamber has been depressurized to a first predetermined pressure; and
wherein in the case where the selection of the low-concentrated mode is received by the receiving means, the transfer means transfers, in a case where the sterilization chamber is depressurized to the first predetermined pressure, the liquid sterilizing agent to the concentration chamber.

5. A sterilization apparatus according to claim 4, further comprising;
    a sensor unit for measuring a pressure in the sterilization chamber; and
    first determination means for determining whether the pressure in the sterilization chamber measured by the sensor has been depressurized to the first predetermined pressure,
    wherein in the case where the selection of the low-concentrated mode is received by the receiving means, the transfer means transfers, in a case where it is determined by the first determination means that the pressure in the sterilization chamber measured by the sensor has been depressurized to the first predetermined pressure, the liquid sterilizing agent to the concentration chamber.

6. A sterilization apparatus according to claim 1,
wherein in the case where the selection of the highly-concentrated mode is received by the receiving means, the sterilization apparatus draws out the liquid sterilizing agent from the concentration chamber at a first timing, and
in the case where the selection of the low-concentrated mode is received by the receiving means, the sterilization apparatus draws out the liquid sterilizing agent from the concentration chamber at a second timing, and
wherein the first timing is different from the second timing.

7. A sterilization apparatus according to claim 1, wherein in the case where the selection of the highly-concentrated mode is received by the receiving means, in a case where a second predetermined condition for drawing out the liquid sterilizing agent from the concentration chamber is satisfied, the sterilization apparatus draws out the liquid sterilizing agent from the concentration chamber to transfer the liquid sterilizing agent from the concentration chamber to the sterilization chamber.

8. A sterilization apparatus according to claim 7, wherein in the case where the selection of the low-concentrated mode is received by the receiving means, the sterilization apparatus draws out the liquid sterilizing agent from the concentration chamber to transfer the liquid sterilizing agent to the sterilization chamber, regardless of whether or not the second predetermined condition is satisfied.

9. A sterilization apparatus according to claim 7, wherein the second predetermined condition includes a condition that indicates whether the sterilization chamber has been depressurized to a second predetermined pressure; and
    wherein, in the case where the selection of the highly-concentrated mode is received by the receiving means, the sterilization apparatus draws out the liquid sterilizing agent from the concentration chamber to transfer the liquid sterilizing agent to the sterilization chamber, in a case where the sterilization chamber is depressurized to the second predetermined pressure.

10. A sterilization apparatus according to claim 9, further comprising:
    second determination means for determining whether pressure in the sterilization chamber measured by the sensor has been depressurized to the second predetermined pressure; and
    wherein, in the case where the selection of the highly-concentrated mode is received by the receiving means, the sterilization apparatus draws out the liquid sterilizing agent from the concentration chamber to transfer the liquid sterilizing agent to the sterilization chamber, in a case where it is determined by the second determination means that the pressure in the sterilization chamber measured by a sensor has been depressurized to the second predetermined pressure.

11. A sterilization apparatus according to claim 9, wherein the second predetermined condition further includes a condition that indicates whether a predetermined time has elapsed from when the liquid sterilizing agent is transferred to the concentration chamber by the transfer means; and wherein, in the case where the selection of the highly-concentrated mode is received by the receiving means, the sterilization apparatus draws out the liquid sterilizing agent from the concentration chamber to transfer the liquid sterilizing agent to the sterilization chamber, in a case where the pressure in the sterilization chamber is depressurized to the second predetermined pressure and the predetermined time has elapsed from when the sterilizing agent is transferred to the concentration chamber.

12. A sterilization apparatus according to claim 11, wherein in the case where the selection of the highly-concentrated mode is received by the receiving means, the sterilization apparatus concentrates the liquid sterilizing agent transferred to the concentration chamber by the transfer means by heating the liquid sterilizing agent for a predetermined period in the concentration chamber, and transfers the concentrated sterilizing agent to a pipe which leads to the sterilization chamber in a case where the sterilization chamber has been depressurized to a predetermined air pressure.

13. A sterilization apparatus according to claim 1, further comprising:

a conduit pipe for exhausting gas generated as a result of the vaporization performed by the heating by the concentration chamber; and a vaporization furnace for vaporizing the liquid sterilizing agent concentrated by being heated by the concentration chamber, wherein the sterilization chamber sterilizes the target objects using the sterilizing gas obtained by vaporizing the liquid sterilizing agent which has been concentrated by being heated by the concentration chamber while the gas generated as a result of the vaporization performed by the heating by the concentration chamber being exhausted to the conduit pipe.

14. A sterilization method for a sterilization apparatus comprising transfer means for transferring, from a container filled with a liquid sterilizing agent, the liquid sterilizing agent to a concentration chamber, the concentration chamber for concentrating the liquid sterilizing agent by applying heat to the liquid sterilizing agent transferred by the transfer means, and a sterilization chamber for sterilizing the target objects using sterilizing gas obtained by vaporizing the liquid sterilizing agent which has been concentrated by being heated by the concentration chamber without using gas generated as a result of vaporization performed by the heating by the concentration chamber, the method comprising:

receiving, from a user via an operation unit, a selection of one mode from among a highly-concentrated mode in which sterilization by using a liquid sterilizing agent highly concentrated in the concentration chamber is performed and a low-concentrated mode in which sterilization by using a liquid sterilizing agent not highly concentrated in the concentration chamber is performed, wherein the liquid sterilizing agent transferred to the concentration chamber by the transfer means is heated by the concentration chamber during a period longer in a case where the selection of the highly-concentrated mode is received by the receiving means than in a case where the selection of the low-concentrated mode is received by the receiving means.

15. A computer program comprising processor executable instructions that upon execution by a processor causes the processor to control a sterilization apparatus so as to perform the method of claim 14.

* * * * *